(12) United States Patent
Bojenko

(10) Patent No.: US 8,969,515 B2
(45) Date of Patent: Mar. 3, 2015

(54) PHARMACEUTICAL COMPOSITION FOR TREATING HYPERPROLIFERATIVE DISEASES

(75) Inventor: Vladimir Konstantinovich Bojenko, Moscow (RU)

(73) Assignee: OOO "MetaMax", Moscow (RU)

(\*) Notice: Subject to any disclaimer, the term of this patent is extended or adjusted under 35 U.S.C. 154(b) by 0 days.

(21) Appl. No.: 14/002,860

(22) PCT Filed: May 20, 2011

(86) PCT No.: PCT/RU2011/000343
§ 371 (c)(1),
(2), (4) Date: Sep. 3, 2013

(87) PCT Pub. No.: WO2012/138246
PCT Pub. Date: Oct. 11, 2012

(65) Prior Publication Data
US 2014/0051644 A1  Feb. 20, 2014

(30) Foreign Application Priority Data
Apr. 6, 2011 (EA) .................................. 201100464

(51) Int. Cl.
| *C07K 7/00* | (2006.01) |
| *A61K 38/00* | (2006.01) |
| *A61K 31/513* | (2006.01) |
| *A61K 31/7048* | (2006.01) |
| *A61K 38/17* | (2006.01) |
| *A61K 47/48* | (2006.01) |

(52) U.S. Cl.
CPC ............. *A61K 38/005* (2013.01); *A61K 31/513* (2013.01); *A61K 31/7048* (2013.01); *A61K 38/1709* (2013.01); *A61K 47/48238* (2013.01); *C07K 2319/00* (2013.01)
USPC ........................................ 530/326; 514/19.3

(58) Field of Classification Search
None
See application file for complete search history.

(56) References Cited

U.S. PATENT DOCUMENTS

| 6,569,833 | B1 * | 5/2003 | Fahraeus et al. ............. 514/19.3 |
| 2002/0142966 | A1 | 10/2002 | Bair et al. |
| 2010/0075892 | A1 | 3/2010 | Zhu et al. |

FOREIGN PATENT DOCUMENTS

| RU | 2297241 | * | 4/2007 |
| RU | 2369402 | | 10/2009 |

OTHER PUBLICATIONS

Kharchenko V.P. Ispolzovanie tekhnologii internalizuemykh peptidov . . . Vestnik RNTSRR MZ RF, M.2004 http://vestnik.mcrr.ru/vestnik/v3/papers/harch7_v3.html, (abstract only).
Kulinich T.M. Issledovanie antiproliferativnoi aktinvnosti . . . M.2006, p. 123.
Data Base, GenBank 1H24_E Feb. 13, 2003.
Data Base, GenBank ACC97479.1 May 5, 2008.
Data Base, GenBank XP002426644 Aug. 3, 2009.
Mitsuno Mayumi et al, Aberrant methylation of p 16 predicts . . . J. Gastroenterol 2007, 42: 866-873.
Supplementary European Search Report dated Sep. 11, 2014 issued in the EP Application No. EP 11863085.

\* cited by examiner

*Primary Examiner* — Sheela J Huff
(74) *Attorney, Agent, or Firm* — Jones Day

(57) ABSTRACT

The proposed pharmaceutical compositions and methods connected thereto relate to the field of biotechnology and medicine, in particular to pharmaceutical compositions having an antiproliferative activity, and to a method of treating oncologic diseases, which includes introducing the aforementioned chimerical peptide into a mammal requiring such treatment. The object of the proposed compositions and methods is the development of a preparation that effectively penetrates the target cells and has a high cytostatic and cytotoxic action.

10 Claims, 33 Drawing Sheets

A

B

A

B

Dependence of cell cycle phases on concentration of peptide p16

A

Dependence of cell cycle phases on concentration of peptide p21

B

A

B

A

B

A

B

A

B

C

D

A

B

A

B

Expression Level of cyclin B

A

Number of cells in G2/M phase

B

```
                         SEQUENCE LISTING

<160> NUMBER OF SEQ ID NOS: 12

<210> SEQ ID NO 1
<211> LENGTH: 20
<212> TYPE: PRT
<213> ORGANISM: Homo Sapiens
<220> FEATURE:
<223> OTHER INFORMATION: functional sequence of protein inhibitor of
      cyclin-kinase p16INK4a

<400> SEQUENCE: 1

Asp Ala Ala Arg Glu Gly Phe Leu Asp Thr Leu Val Val Leu His Arg
1               5                   10                  15

Ala Gly Ala Arg
            20

<210> SEQ ID NO 2
<211> LENGTH: 16
<212> TYPE: PRT
<213> ORGANISM: Homo Sapiens
<220> FEATURE:
<223> OTHER INFORMATION: pAntp

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 37
<212> TYPE: PRT
<213> ORGANISM: Homo Sapiens
<220> FEATURE:
<223> OTHER INFORMATION: pANTp_p16(2), chimeric peptide

<400> SEQUENCE: 3

Asp Ala Ala Arg Glu Gly Phe Leu Asp Thr Leu Val Val Leu His Arg
1               5                   10                  15

Ala Gly Ala Arg Ser Arg Gln Ile Lys Ile Trp Phe Gln Asn Arg Arg
            20                  25                  30

Met Lys Trp Lys Lys
        35

<210> SEQ ID NO 4
<211> LENGTH: 83
<212> TYPE: PRT
<213> ORGANISM: Homo Sapiens
<220> FEATURE:
<223> OTHER INFORMATION: pANTp_p16(3), chimeric peptide

<400> SEQUENCE: 4

Arg Gly Ser Asp Ala Ala Arg Glu Gly Phe Leu Asp Thr Leu Val Val
1               5                   10                  15

Leu His Arg Ala Gly Ala Arg Gln Ile Lys Ile Trp Phe Gln Asn
            20                  25                  30

Arg Arg Met Lys Trp Lys Lys Ser Glu Arg Lys Arg Gly Arg Gln Thr
        35                  40                  45
```

Tyr Thr Arg Tyr Gln Thr Leu Glu Leu Glu Lys Glu Phe His Phe Asn
            50                  55                  60

Arg Tyr Leu Thr Arg Arg Arg Ile Glu Ile Ala His Ala Leu Cys
65                  70                  75                  80

Leu Thr Glu

<210> SEQ ID NO 5
<211> LENGTH: 12
<212> TYPE: PRT
<213> ORGANISM: Homo Sapiens
<220> FEATURE:
<223> OTHER INFORMATION: Tat, internalizable sequence

<400> SEQUENCE: 5

Tyr Gly Arg Lys Lys Arg Arg Gln Arg Arg Arg Gly
1               5                   10

<210> SEQ ID NO 6
<211> LENGTH: 8
<212> TYPE: PRT
<213> ORGANISM: Homo Sapiens
<220> FEATURE:
<223> OTHER INFORMATION: functional sequence of protein inhibitor of
      cyclin-kinase p21/CIP/KIP

<400> SEQUENCE: 6

Pro Val Lys Arg Arg Leu Asp Leu
1               5

<210> SEQ ID NO 7
<211> LENGTH: 33
<212> TYPE: PRT
<213> ORGANISM: Homo Sapiens
<220> FEATURE:
<223> OTHER INFORMATION: Tat_p16, chimeric peptide

<400> SEQUENCE: 7

Asp Ala Ala Arg Glu Gly Phe Leu Asp Thr Leu Val Val Leu His Arg
1               5                   10                  15

Ala Gly Ala Arg Ser Tyr Gly Arg Lys Lys Arg Arg Gln Arg Arg
            20                  25                  30

Gly

<210> SEQ ID NO 8
<211> LENGTH: 20
<212> TYPE: PRT
<213> ORGANISM: Homo Sapiens
<220> FEATURE:
<223> OTHER INFORMATION: Tat_p21, chimeric peptide

<400> SEQUENCE: 8

Tyr Gly Arg Lys Lys Arg Arg Gln Arg Arg Gly Pro Val Lys Arg
1               5                   10                  15

Arg Leu Asp Leu
            20

<210> SEQ ID NO 9
<211> LENGTH: 44
<212> TYPE: PRT
<213> ORGANISM: Homo Sapiens
<220> FEATURE:
<223> OTHER INFORMATION: Insert for pAntp_p16(3)

```
<400> SEQUENCE: 9

Ser Glu Arg Lys Arg Gly Arg Gln Thr Tyr Thr Arg Tyr Gln Thr Leu
1               5                   10                  15

Glu Leu Glu Lys Glu Phe His Phe Asn Arg Tyr Leu Thr Arg Arg Arg
            20                  25                  30

Arg Ile Glu Ile Ala His Ala Leu Cys Leu Thr Glu
        35                  40

<210> SEQ ID NO 10
<211> LENGTH: 36
<212> TYPE: PRT
<213> ORGANISM: Homo Sapiens
<220> FEATURE:
<223> OTHER INFORMATION: pAntp_p16(1), chimeric peptide

<400> SEQUENCE: 10

Arg Gln Ile Lys Ile Trp Phe Gln Asn Arg Arg Met Lys Trp Lys Lys
1               5                   10                  15

Asp Ala Ala Arg Glu Gly Phe Leu Asp Thr Leu Val Val Leu His Arg
            20                  25                  30

Ala Gly Ala Arg
        35

<210> SEQ ID NO 11
<211> LENGTH: 20
<212> TYPE: PRT
<213> ORGANISM: Homo Sapiens
<220> FEATURE:
<223> OTHER INFORMATION: p16INK4a_zam

<400> SEQUENCE: 11

Asp Ala Ala Arg Glu Gly Phe Leu Asp Ala Leu Val Val Leu His Arg
1               5                   10                  15

Ala Gly Ala Arg
            20

<210> SEQ ID NO 12
<211> LENGTH: 36
<212> TYPE: PRT
<213> ORGANISM: Homo Sapiens
<220> FEATURE:
<223> OTHER INFORMATION: pAntp_zam, chimeric peptide

<400> SEQUENCE: 12

Arg Gln Ile Lys Ile Trp Phe Gln Asn Arg Arg Met Lys Trp Lys Lys
1               5                   10                  15

Asp Ala Ala Arg Glu Gly Phe Leu Asp Ala Leu Val Val Leu His Arg
            20                  25                  30

Ala Gly Ala Arg
        35
```

PHARMACEUTICAL COMPOSITION FOR TREATING HYPERPROLIFERATIVE DISEASES

CROSS-REFERENCE TO RELATED APPLICATIONS

This application is a U.S. national stage application of a PCT application PCT/RU2011/000343 filed on 20 May 2011, published as WO/2012/138246, whose disclosure is incorporated herein in its entirety by reference, which PCT application claims priority of a EAPO application EA201100464 filed on 6 Apr. 2011.

FIELD OF THE INVENTION

The present invention relates to biotechnology, and medicine, particularly to pharmaceutical compositions for the treatment of hyperproliferative diseases, including cancer, which possesses antiproliferative activity and includes a) a chimeric peptide comprising a functional sequence of a protein inhibitor of cyclin-kinase p16INK4a (SEQ ID NO: 1) or p21/CIP/KIP (SEQ ID NO: 6) and a transport sequence, which are linked by a group X, wherein X represents an amino acid sequence comprising from 1 to 50 amino acid residues. b) a therapeutically active agent selected from the group comprising of 5-fluorouracil, etoposide; c) a pharmaceutically acceptable carrier.

The invention also relates to the use of above pharmaceutical compositions for treating cancer, and to a method of treating cancer, including administering said pharmaceutical composition to a mammal in need of such treatment. The object of the invention is to provide a drug which effectively penetrates into target cells and possesses high cytotoxic and cytostatic effects.

BACKGROUND OF THE INVENTION

Since the early 90s more than 400,000 cases of malignant neoplasms are diagnosed in Russia each year. At the same time in Europe, the annual death rate from cancer in the period from 1985 to 2002 continues to grow. Among the causes of mortality cancer occupies second place after diseases of the cardio-vascular system. Therefore the search for new anticancer drugs is one of the most urgent problems of modern biology and medicine.

Currently there is a large number of works devoted to the development of novel drug anticancer drugs based on advances in molecular biology (Richard J P et al., 2003; Takeshima K. et al., 2003; Jyotika A. et al., 2005 Kopnin B P, 2000). It is generally accepted that the fundamental feature of the neoplastic cells is a violation of the regulation of the cell cycle and apoptosis (Chappuis P O, Kapusta L., 2005). It is known that the regulation of cell proliferation processes is controlled by sequential activation of the respective cyclins and cyclin-dependent kinases (CDK).

Cyclin kinase activity is determined by the level of expression of cyclins and relevant activity of specific inhibitors of cyclin kinases (Kastan M V, Bartek J., 2004). There are several families of cyclin kinase inhibitors. The most studied and practically important among them are p16INK4a, p21/CIP/KIP, p27 KIP1 (Lowe S W et al., 2004). Mutations or hypermethylation of promoters of cyclin kinases inhibitor genes are observed in 40-60% of cases of malignant lymphomas, pancreatic cancer and in other malignancies (Sawyers C., 2004; Ortega S. et al, 2002).

Based on these results there was synthesized a number of small molecule inhibitors of cyclin kinases, part of which is now under experimental study (Ross M F, Murphy M R, 2004) and one of which, UCN-1, is in phase one of clinical trials. Another possible direction to generate cyclin kinase inhibitors may be to use functional sequences of the respective intracellular inhibitors (Ziegler A. et al., 2005). Protein p16INK4a is one of the most interesting candidate inhibitors of Cdk (Xu D. et al., 2004; Zhang Y. et al., 2005).

It is known that protein p16INK4a inhibits cyclin D-dependent kinases and thus inhibits G1 phase of the cell cycle (Fu G H et al., 2005; Ben-Saadon R. et al., 2004). It is shown that its function is impaired in a wide range of cancer types (Li J Q et al., 2004). Recently, experimental works started to appear describing the use of gene p16INK4a for gene therapy of tumors of various origins (Lee A W C, Li J H et. Al. 2003; Liu S. X, Tang S. Q, Liang C. Y. 2003; Zhang Y., Liu J. et al. 2005). An additional incentive to seek technologies of applying natural protein proliferation inhibitors was the discovery of short sequences of amino acids (n=15-30) capable of performing vector (transport) functions in respect of peptide sequences and compounds of other chemical nature (RNA, DNA) (Fawell S., Seery J. et al., 1994; Vives E., Brodin P., Lebleu B. 1997; Kaplan I M et al., 2005; Gupta B. et al, 2005; Feraandez-Cameado J. et al., 2005). So far, attempts were made to solve the problem of restoring the impaired function of intracellular proteins by the methods of gene transfer (gene therapy). However, this technology has yet to gain wide use in clinical practice due to a number of fundamental problems.

An alternative way to solve this problem, which is based on the technology of peptide vectors that are able to penetrate cells without damaging the plasma membrane, is very promising due to the weak immunogenicity of such compounds, and the ability to carry quite large molecules.

Combination of capabilities of targeted delivery of peptides into the cell and discovery of short functional domains in protein regulators of various cellular functions set the stage for the design of molecules with pathogenetic orientation (Schutze-Redelmeier M R et al, 2004; Trehin R., Merkle N R, 2004; Cong-Mei Wu et al, 2004). The relative ease of synthesis of these molecules suggests the general possibility for creating individual chemotherapy based on them, i.e., influencing the pathological changes which are characteristic of a particular tumor (Perea S. E. et al, 2004).

The discovery of peptides that are capable to penetrate into the cell without the participation of the membrane proteins and provide for intracellular transport of protein fragments and oligonucleotides linked thereto, opens a new stage in the development of biology and medicine. One of the most effective transporters of large molecules into the cells is the peptide pAntp. Its properties are known, in particular from publications by Derossi D. et al. The third helix of the Antennapedia homeodamain translocates through membranes.//J.Biol. Chem. 269 (1994) 10444-10450 and Morris M C. et al. A peptides carrier for the delivery of biologically active proteins in mammalian cells.//Nat. Biotechnology. 19 (2001) 1173-1176.

The document U.S. Pat. No. 6,569,833 B1 (Cyclacel Limited, GB) discloses peptides that bind to cyclin kinases and include amino acid residues 84-103 of full-chain p16 protein and can be combined with a sequence of a transport protein penetratine by a disulfide bond formed between cysteine residues, especially attached to the C-terminus of the peptide p16 and N-terminus of the peptide pAntp. The disadvantage of this approach is the need for a selective and multi-step synthesis of a chimeric molecule that complicates the way of obtaining the desired product and increases the overall time required for synthesis.

Cited publications indicate that the inhibition of cyclin kinases can be of decisive importance for gene therapy of tumors of various origins. Regarding therapeutic agents based on peptides that bind to cyclin kinase and are combined with a sequence of transport protein, there are certain problems associated with the bioavailability and stability. Therefore, there exists the need to develop new therapeutic agents that have antiproliferative activity against certain types of cancer.

An objective of present invention is to obtain a pharmaceutical composition possessing anti-proliferative and cytotoxic activity due to expressed synergistic effect of a combined use of a chimeric peptide and existing anti-tumor chemotherapeutic agents, such as taxol, 5-fluorouracil, etoposide.

The utility effect of the present invention is an improvement of the biological effect of an agent as compared to solutions known in the art, reflected in the enhancement of cytotoxic and cytostatic effects of the agent on tumor cells.

The utility effect is achieved by a pharmaceutical composition having anti-proliferative and cytotoxic activity, which comprises two active agents, wherein the first active agent is a chimeric peptide comprising a functional sequence of a protein inhibitor of cyclin kinases p16INK4a (SEQ ID NO: 1) of 20 amino acid in length, or an amino acid sequence of protein inhibitor p21/CIP/KIP (SEQ ID NO: 6) and a transport sequence. The second active agent is a chemotherapeutic anticancer agent selected from the group consisting of taxol, 5-fluorouracil, etoposide.

In a preferred embodiment, the pharmaceutical composition is intended for the treatment of cancer selected from the group consisting of colorectal cancer, renal cancer, lung cancer, breast cancer, bladder cancer, pancreatic cancer, uterine cancer, prostate cancer, stomach cancer and ovarian cancer.

In a most preferred embodiment, the pharmaceutical composition may be used for the treatment of colorectal cancer.

In another embodiment, the present invention relates to the use of said pharmaceutical composition for the manufacture of a medicament for the treatment of cancer.

In a preferred embodiment, said pharmaceutical composition can be used for the treatment of cancer selected from the group consisting of colorectal cancer, renal cancer, lung cancer, breast cancer, bladder cancer, pancreatic cancer, uterine cancer, prostate cancer, stomach cancer and ovarian cancer.

In another embodiment, the present invention relates to a method of treating cancer which comprises administering the aforementioned pharmaceutical composition to a mammal in need of such treatment.

In a preferred embodiment of the aforementioned method, the cancer is selected from the group consisting of colorectal cancer, renal cancer, lung cancer, breast cancer, bladder cancer, pancreatic cancer, uterine cancer, prostate cancer, stomach cancer and ovarian cancer.

(A) and p16 (B) active centers. Incubation time is 24 hours. The maximum difference between the control and test samples for p21 is 10-12 hours, for p16 is 8-10 hours. The mean values are based on six successful experiments.

Figure 16:
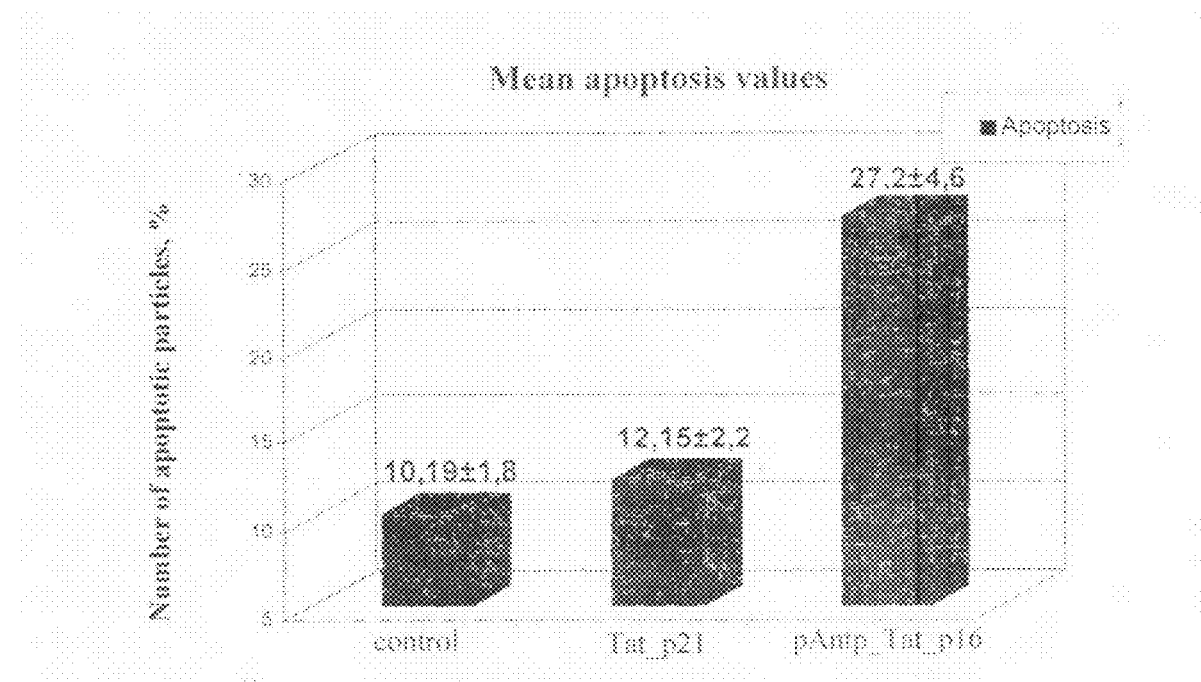

FIG. 16. Mean apoptosis values for synchronized HEK293 cell culture in a series of experiments using internalized peptides with active centers p21 and p16. Incubation time with peptide is 24 hours. Concentration of peptides is 40 .mu.Mol. Y-axis—percentage of apoptotic particles.

Figure 17:
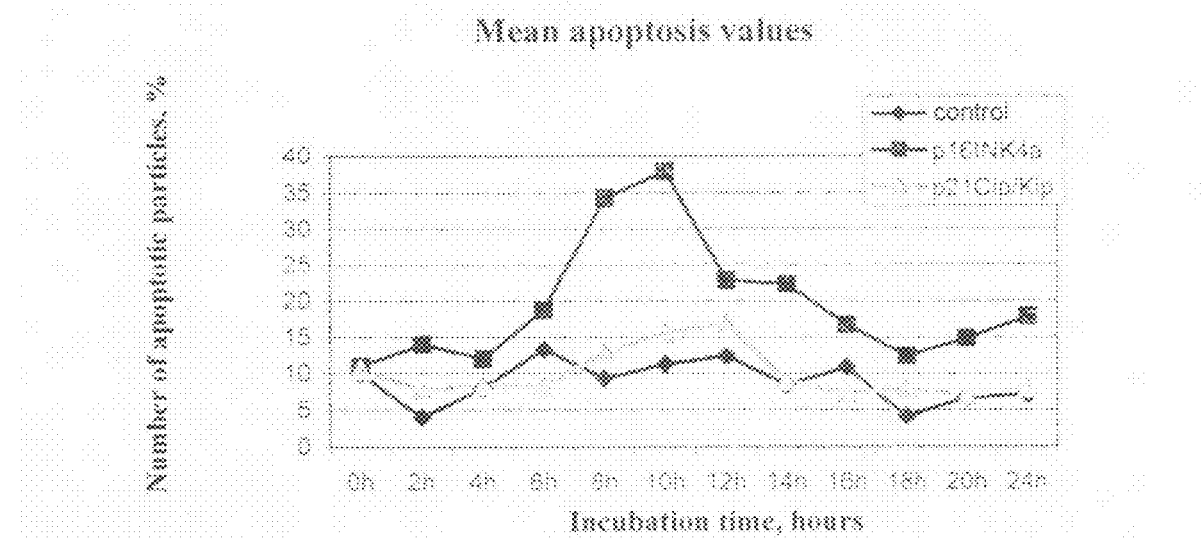

FIG. 17. Mean apoptosis levels in dependence on the incubation time for control samples, samples with a p16INK4a fragment and samples with a p21 fragment. X-axis—incubation time, Y-axis—percentage of apoptotic particles. The FIG. reveals a distinct maximum in the level of apoptosis in samples with peptides having an active p16 center after 10 hours of incubation.

Figure 18:
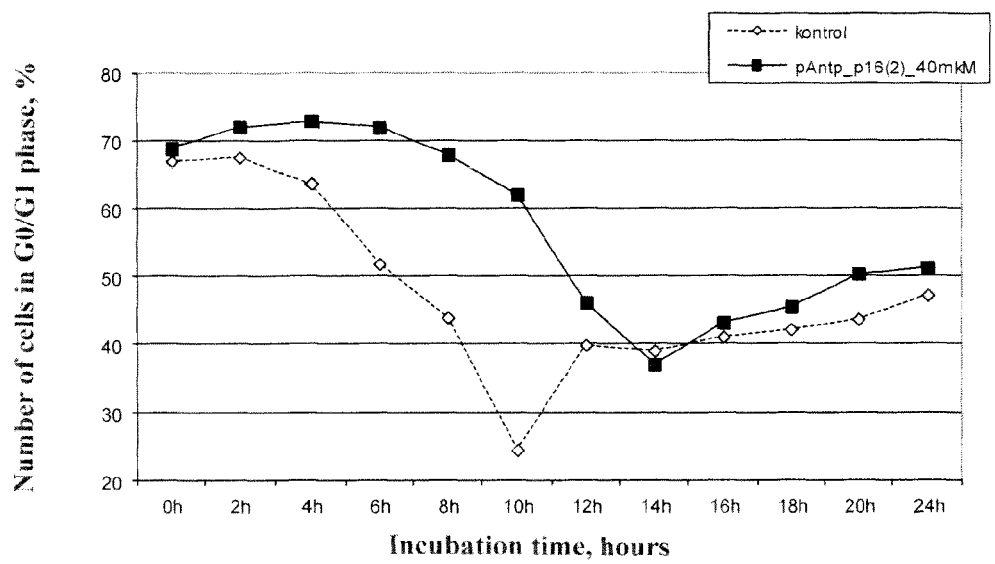
Figure 18:
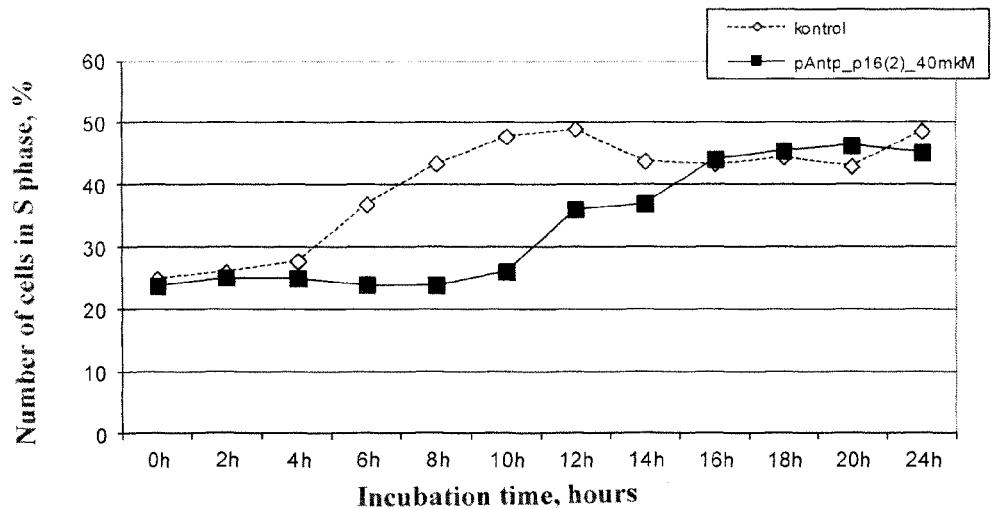
Figure 18:
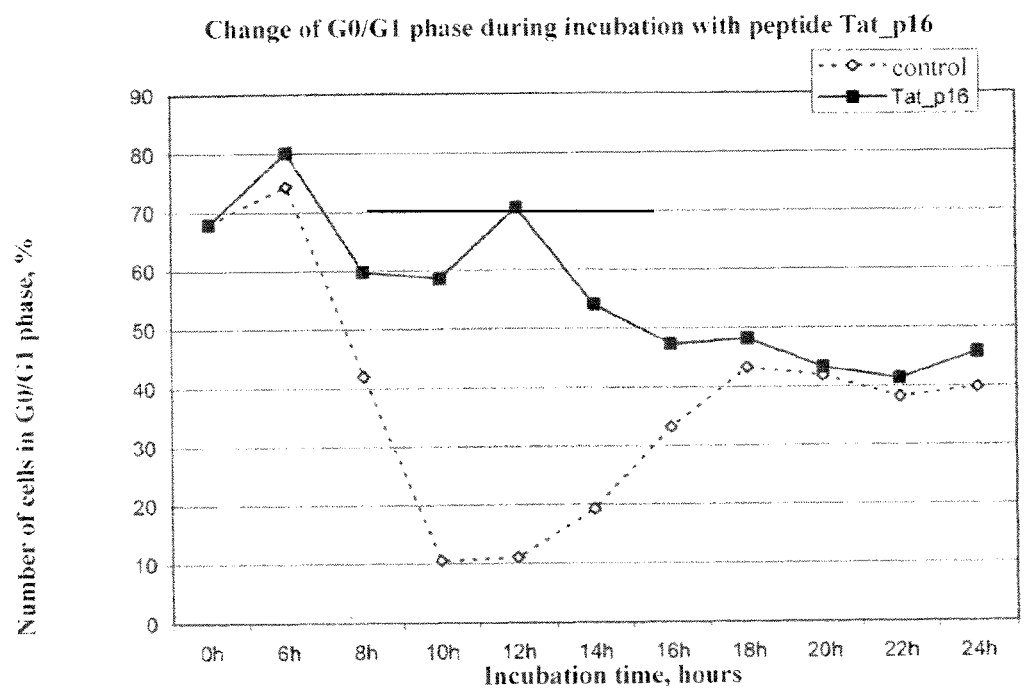
Figure 18:
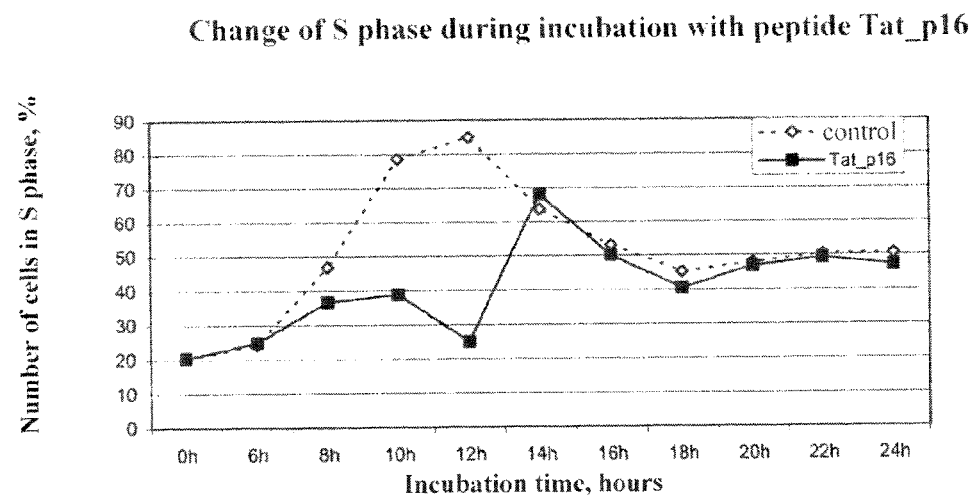

FIG. 18. Effect of chimeric peptides with a p16INK4a functional group on cell cycle. Mean values of 5 successful experiments for peptide pAntp p16 (A—G0/G1 phase change during the incubation of cells with chimeric peptide pAntpp16, B—S phase change, concentration of peptide is 40 .mu.Mol) and mean values of 3 successful experiments for peptide Tat_p16 (C—G0/G1 phase change during the incubation of cells with chimeric peptide Tat_p16, D—S phase change, concentration of peptide is 40 .mu.Mol).

Figure 19:
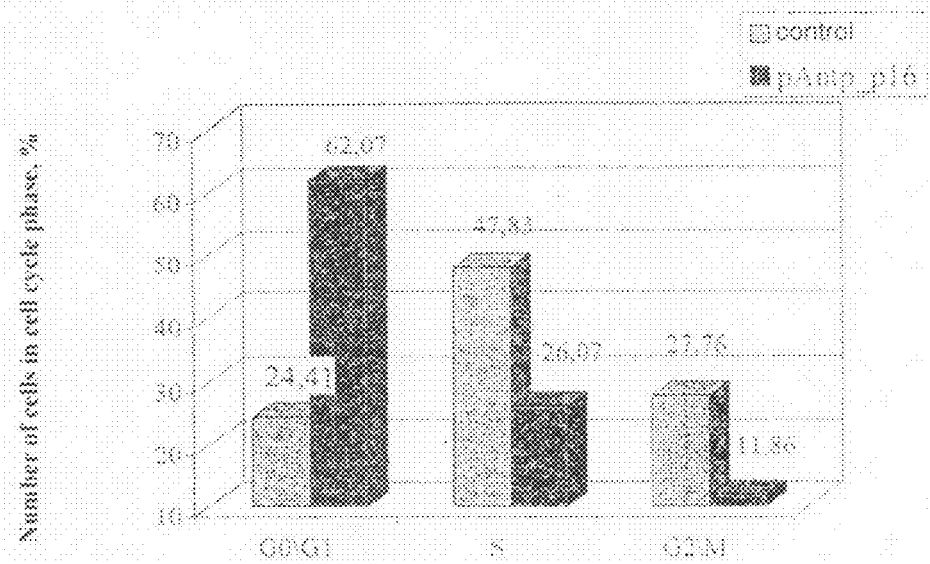
Figure 19:
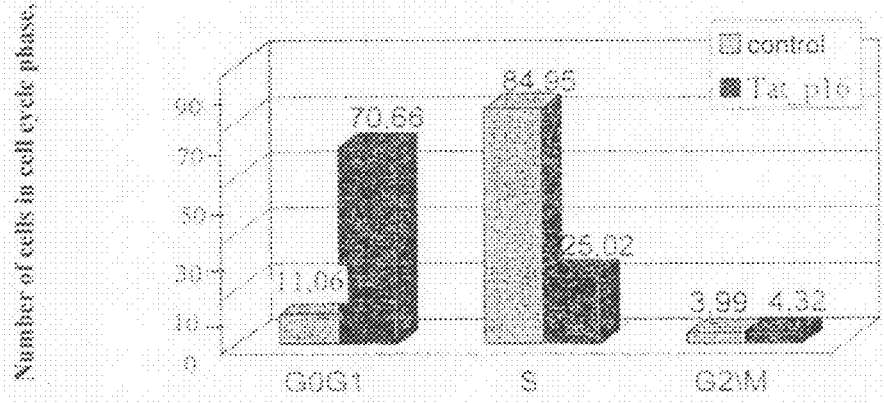

FIG. 19. Distribution of cell cycle phases for synchronized HEK293 cell line after addition of chimeric peptides with an p16 active center and peptide vectors pAntp (FIG. 19A) and Tat (FIG. 19B). The time point of maximum difference between the control and test samples for pAntpp16 is 10 hours and for Tatp16 is 12 hours. Mean values for six experiments. Concentration of peptides is 40 .mu.M.

Figure 20:
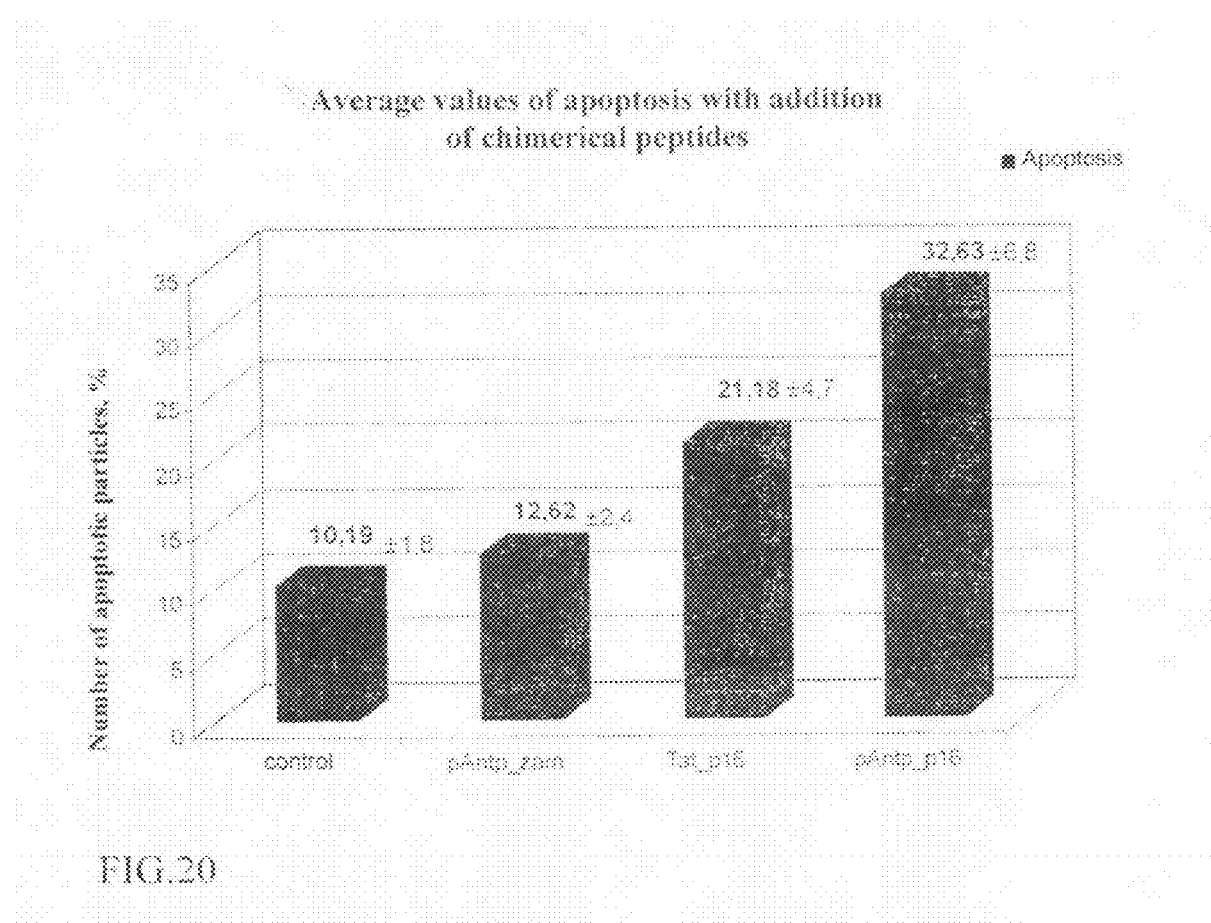

FIG. 20. Mean apoptosis values in synchronized culture of HEK293 after addition of chimeric peptides Tat_p16 and pAntp p16. The figure shows the level of apoptosis detected after the removal of a synchronization block in HEK293 cell culture synchronized in G0/G1-phase. The peptides were added at the moment of synchronization block removal. The effect was evaluated after 24 hours.

Figure 21:
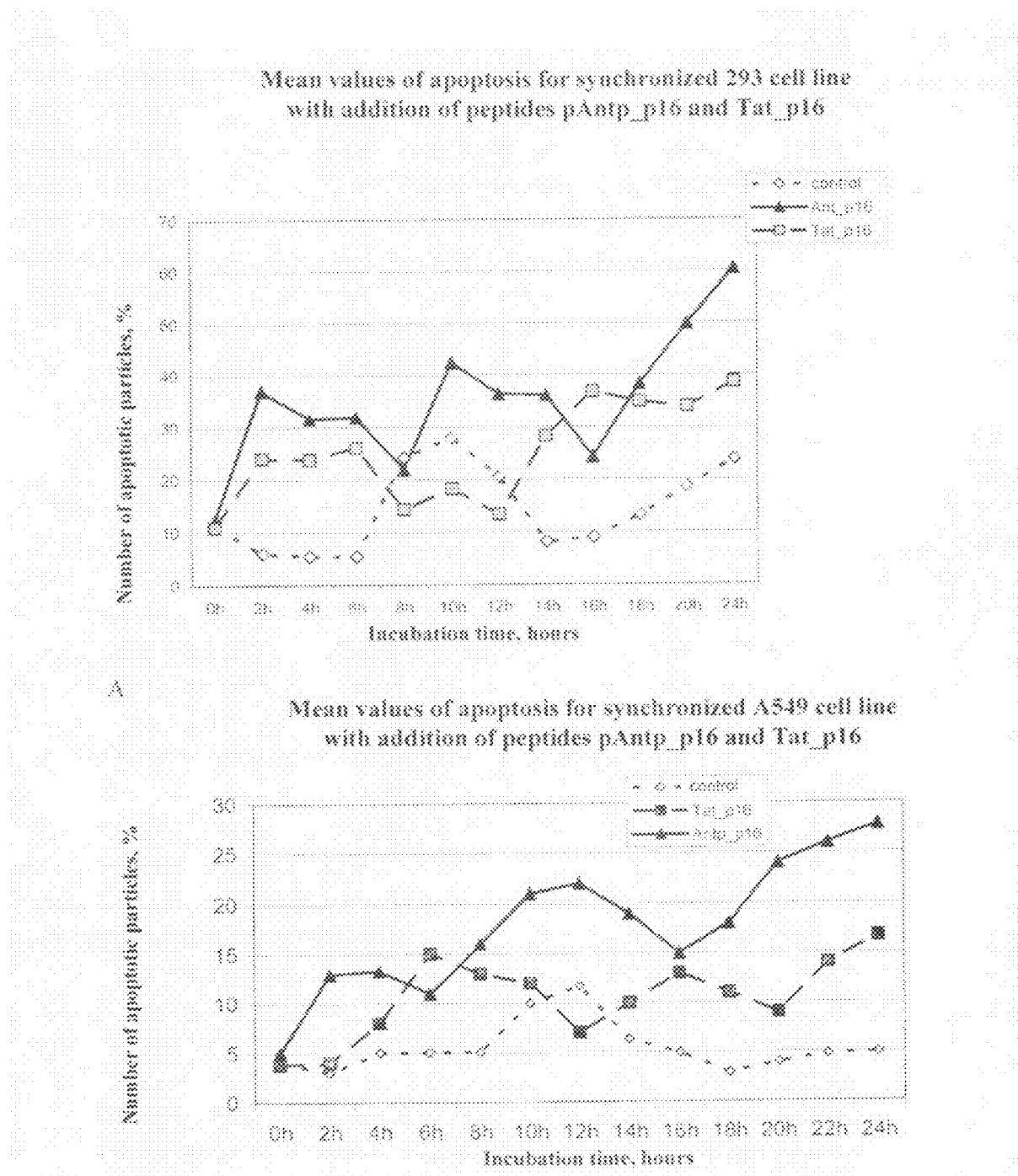

FIG. 21. Change in the level of apoptosis in the cell culture depending on the incubation time with peptides Tat_p16 and pAntp_p16 for synchronized 293 cell line (A) and synchronized A549 cell line (B).

Figure 22:
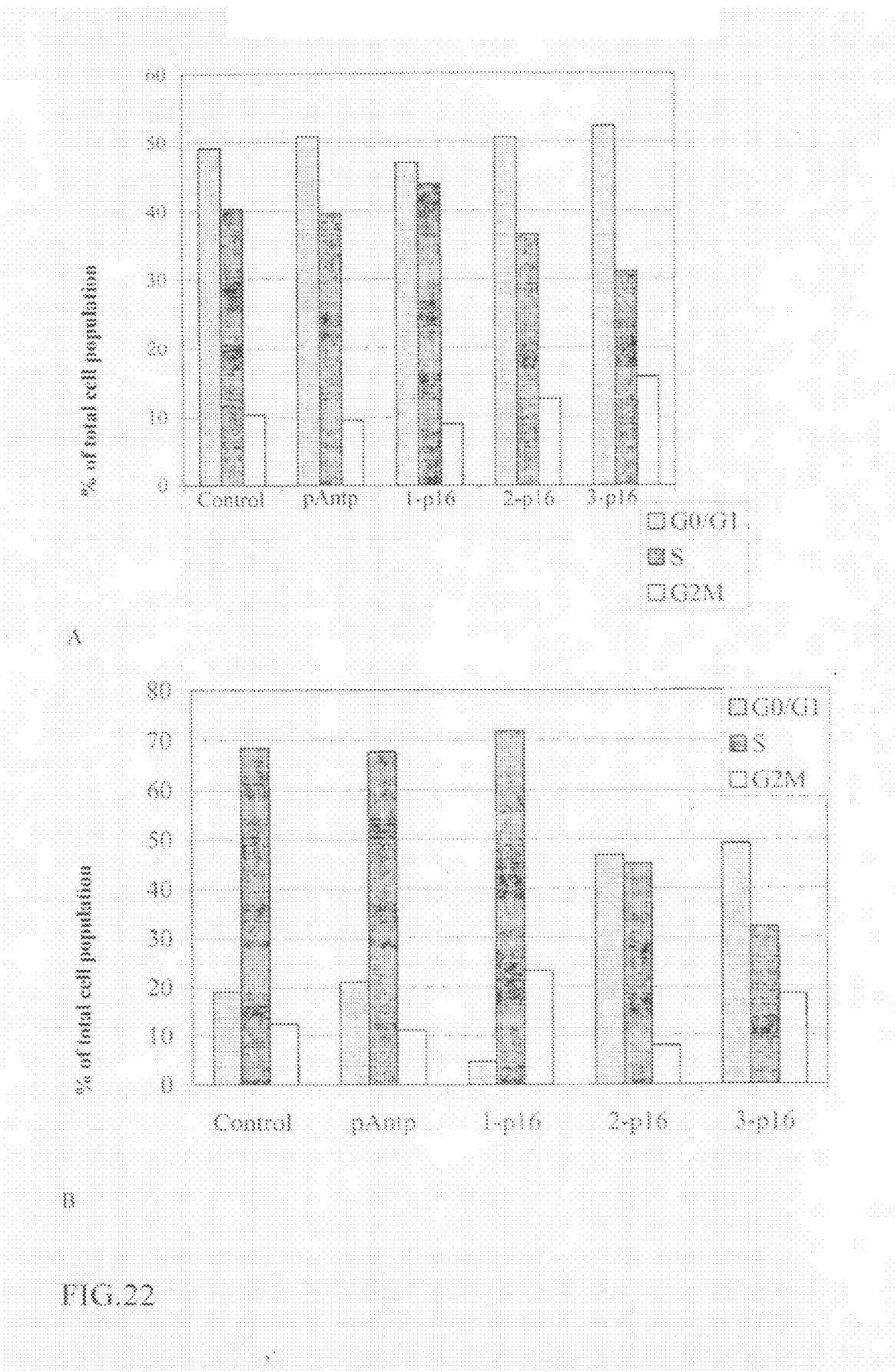

FIG. 22. Effect of chimeric peptide pAntp containing a p16INK4a fragment, on the cell cycle. A—non-synchronized cell line HEK293, B—cell line HEK293 synchronized in S-phase. Peptide concentration is 40 .mu.M. The peptides are pAntp and three further peptides 1-p16, 2-p16, and 3-p16, wherein peptides 1-p16 and 2-p16 are synthetic peptides differing by the location of the 20 amino acids fragment of p16 relative to pAntp; and peptide 3-p16 is a genetically engineered peptide comprising a 50 amino acids insert of protein Antp.

Figure 23:
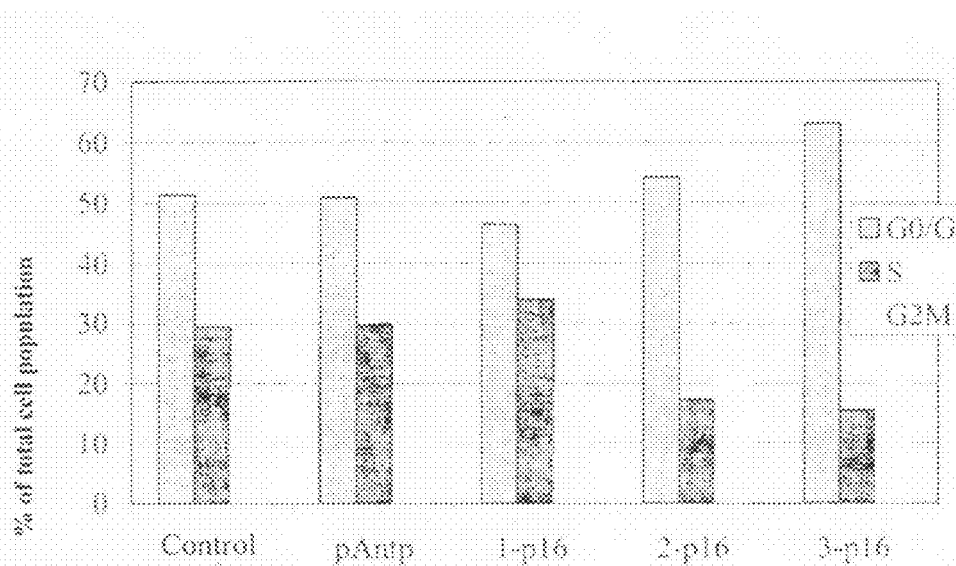
Figure 23:
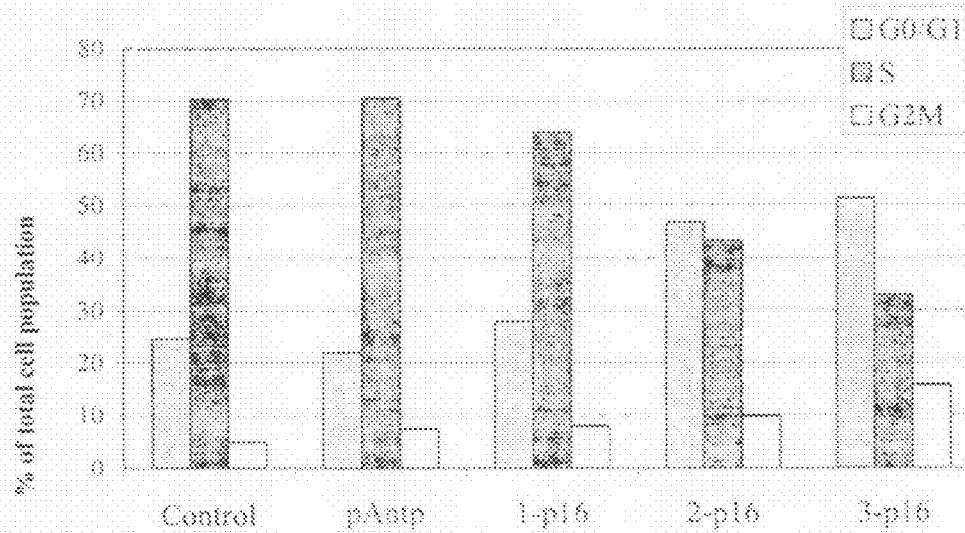

FIG. 23. Effect of chimeric peptides pAntp comprising a p16INK4a fragment on the cell cycle. A—non-synchronized cell line 549, B—synchronized cell line 549. Peptide concentration is 40 .mu.M. pAntp-pAntp_zam.

Figure 24:
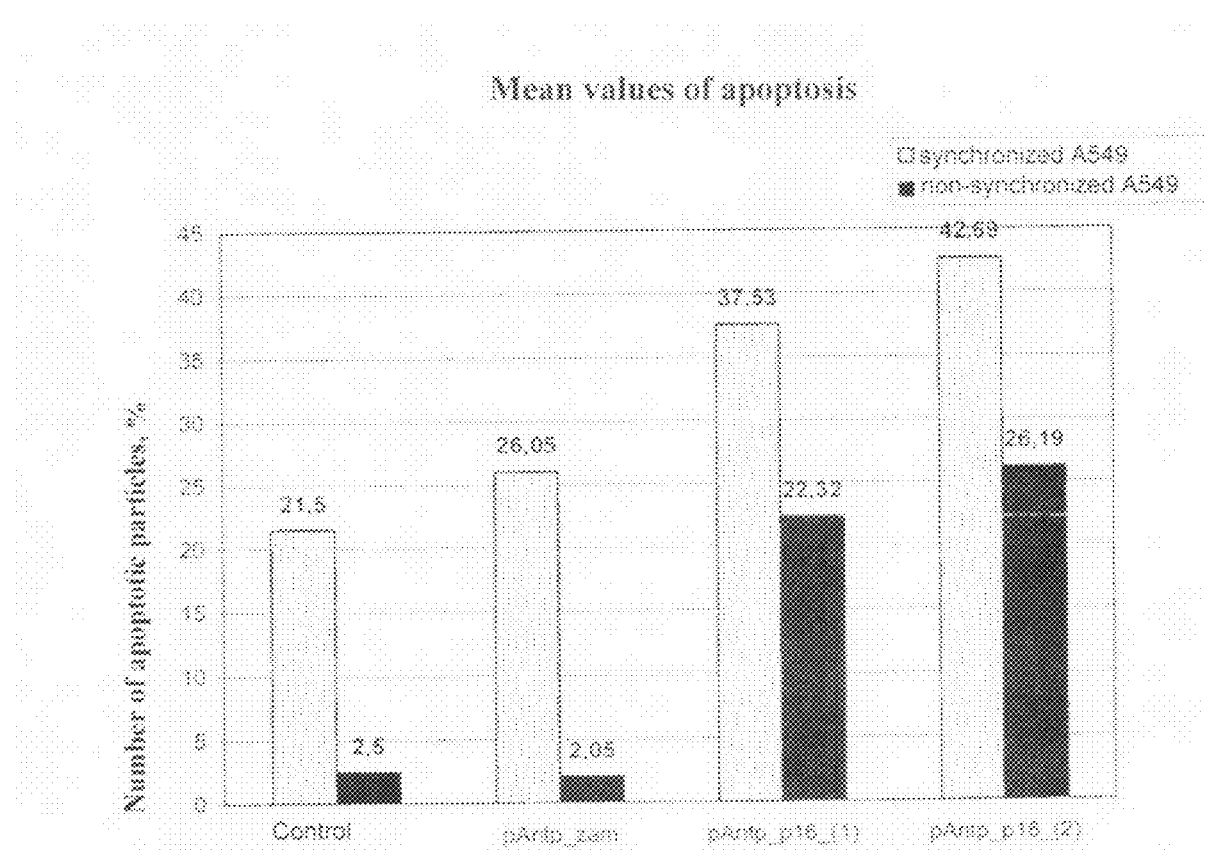

FIG. 24. Effect of chimeric peptides containing a p16INK4a fragment on apoptosis level in non-synchronized and synchronized cell line A549. Peptide concentration is 40 .mu.M. Y-axis—percentage of apoptotic bodies.

Figure 25:
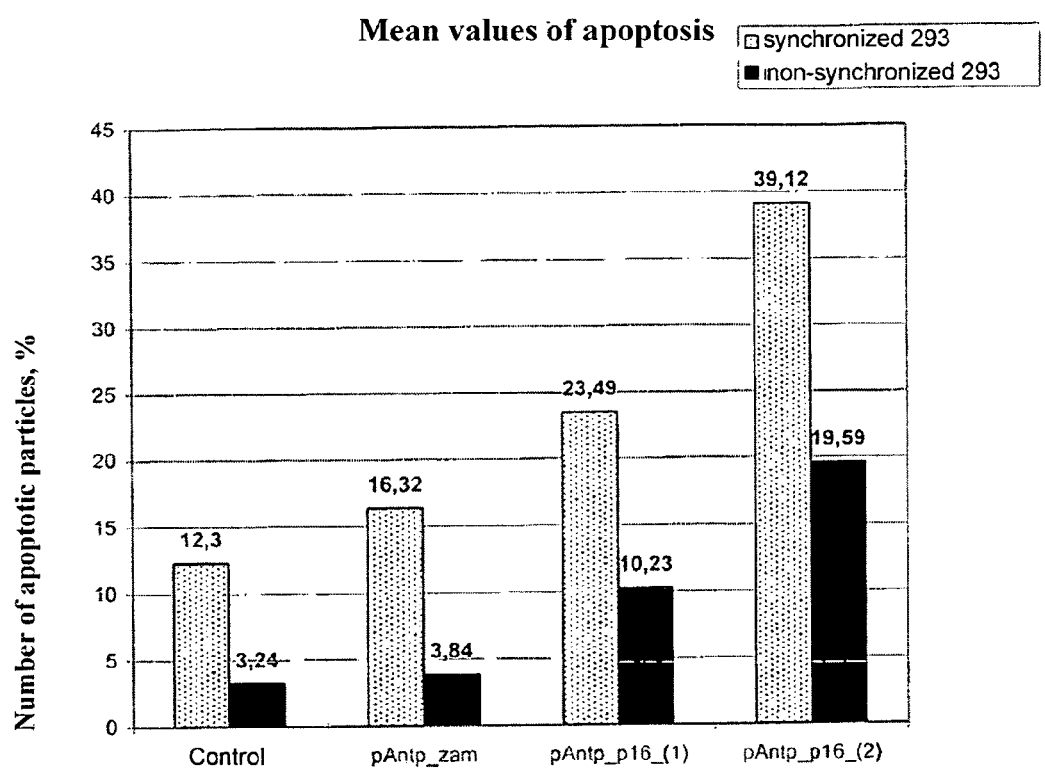

FIG. 25. Effect of chimeric peptides containing a p16INK4a fragment on apoptosis level in non-synchronized and synchronized HEK293 cell line. Peptide concentration is 40 .mu.M. Y-axis—percentage of apoptotic bodies.

Figure 26:
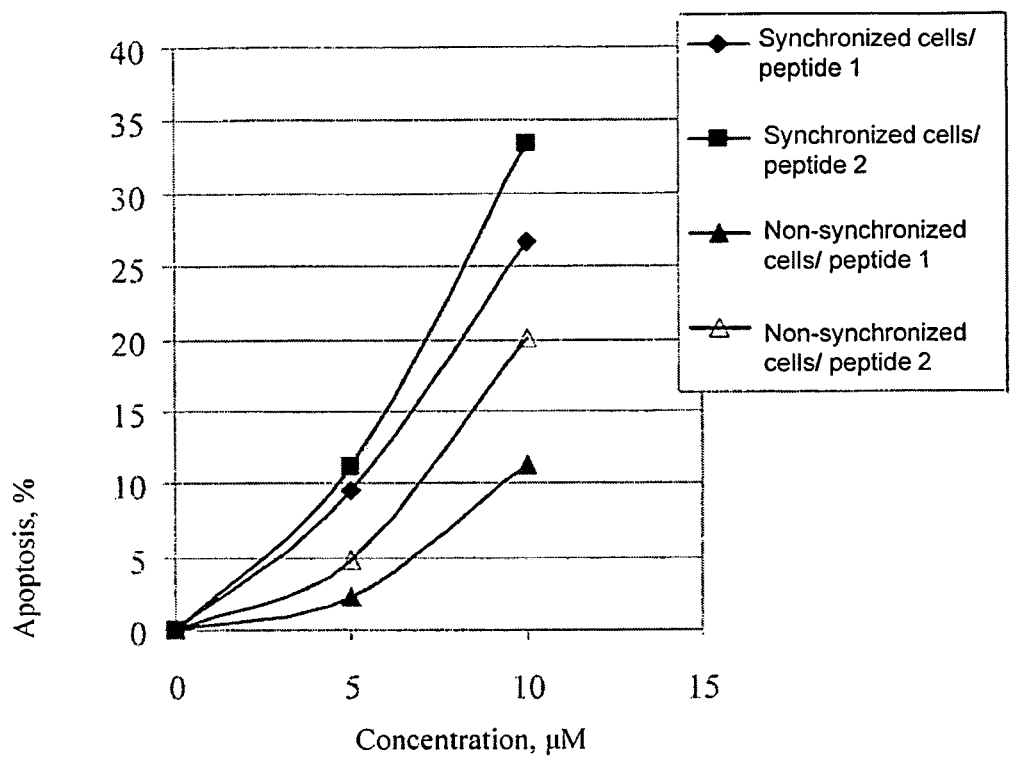

FIG. 26. Comparisons of cytotoxic effect of chimeric peptides pAntpp16 (1, 2) on HEK293 cell culture.

Figure 27:
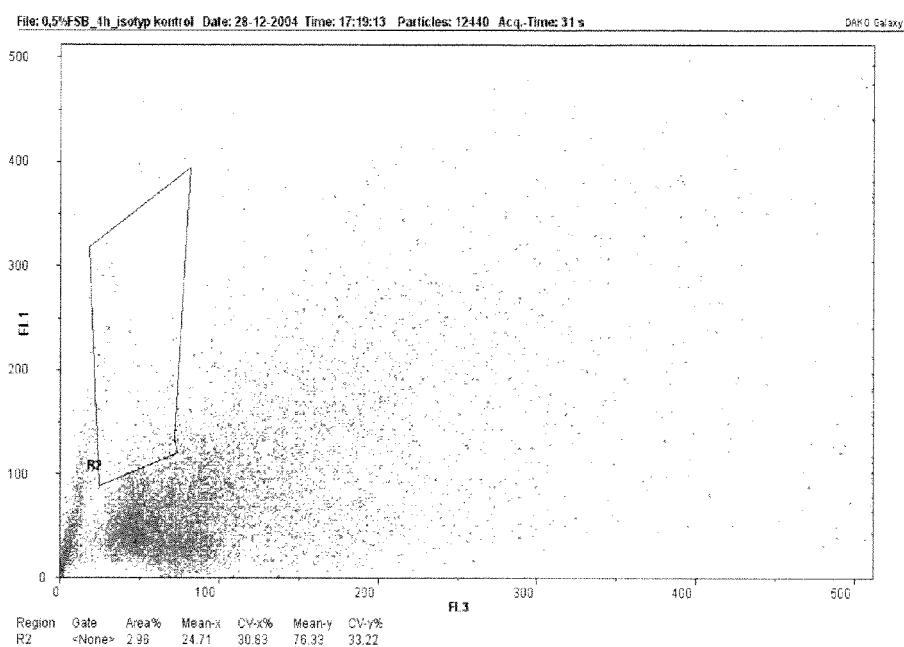
Figure 27:
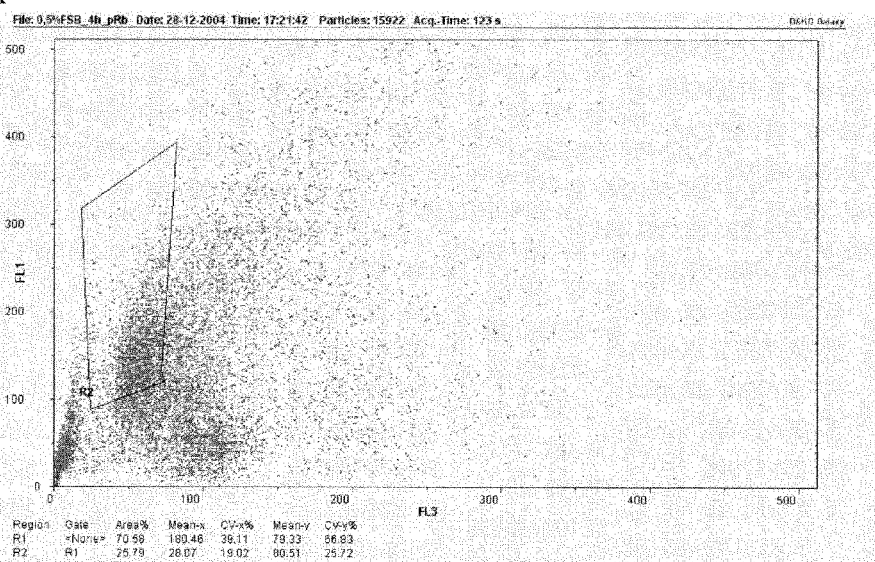

FIG. 27. Changes in the level of antibody binding to underphosphorylated pRB obtained by flow cytometry. A549 cell line is synchronized by depleted medium 4 hours after the removal of a synchronization block. A—isotype control, B—pRb staining Area of cells in which Rb is in phosphorylated state is indicated. Control sample.

Figure 28:
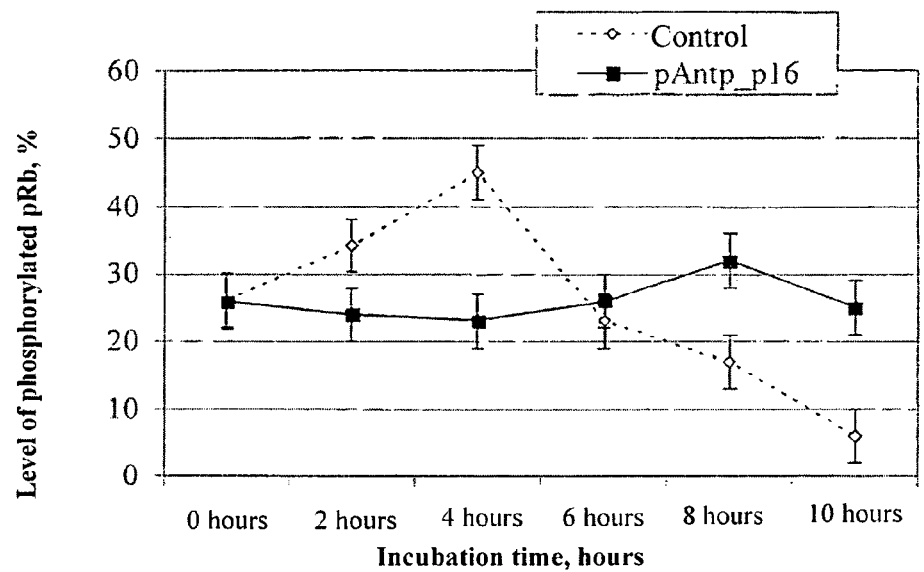
Figure 28:
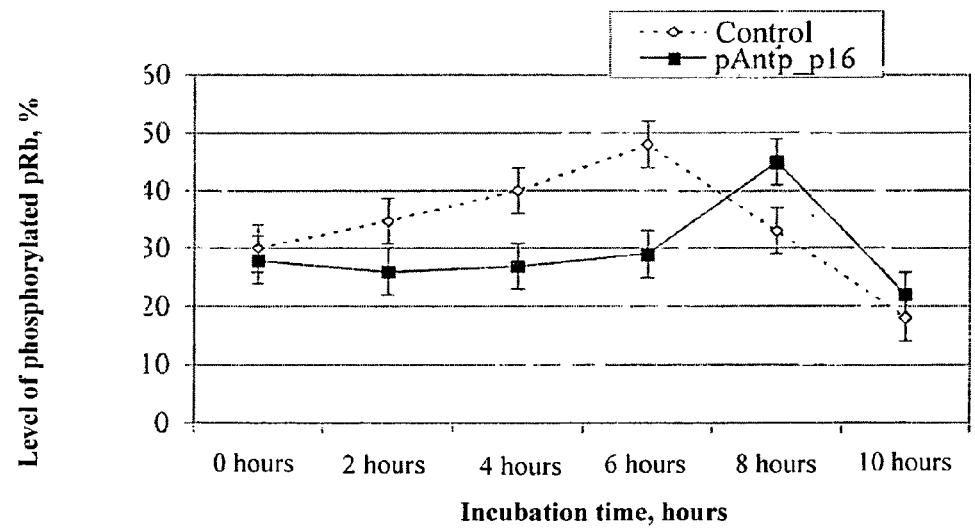

FIG. 28. Percentage of phosphorylated pRb as function of incubation time for control samples and samples with peptide pAntp_p16 (40 .mu.M). A—A549 cell line, B—HEK293 cell line. X-axis—incubation time (hours), Y-axis—percentage of cells with phosphorylated pRb.

Figure 29:
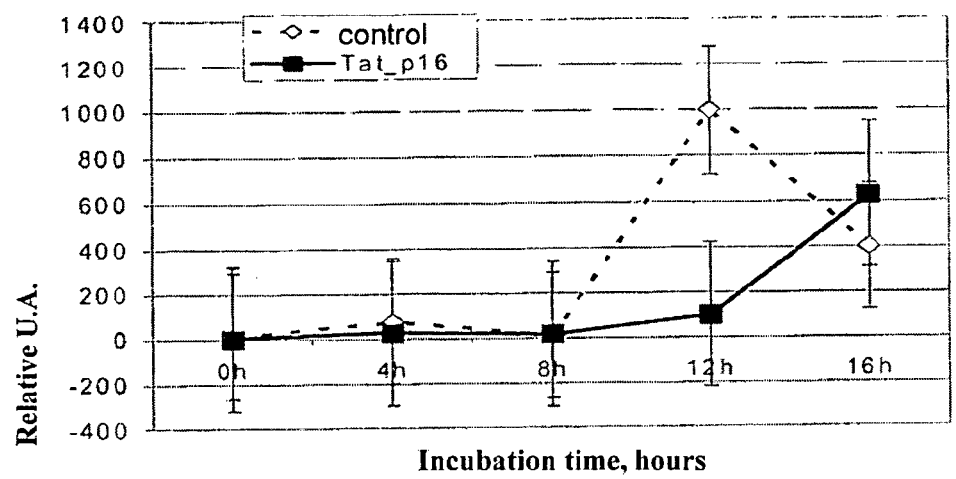
Figure 29:
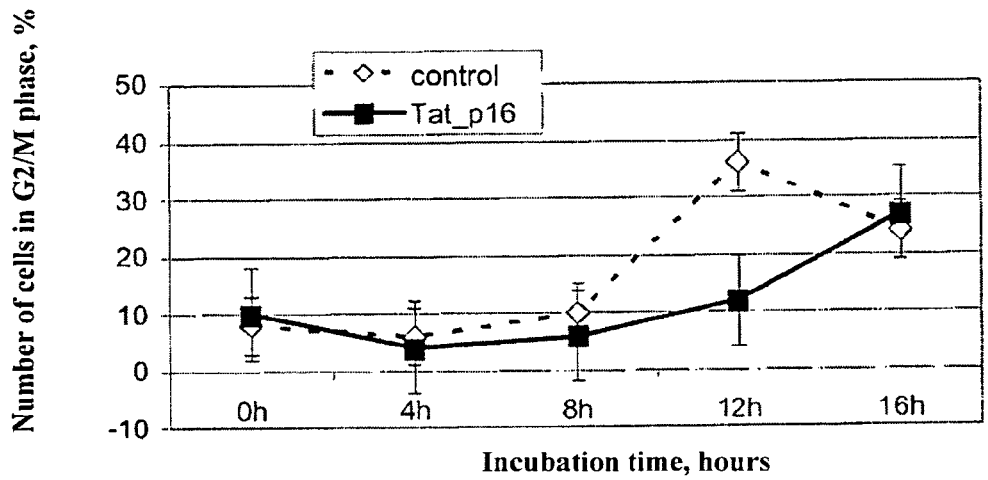

FIG. 29. Study of cyclin B synthesis in HEK293 cell culture by adding peptide Tat_p16 (30 .mu.Mol). FIG. 29A shows change in the level of cyclin B in a control sample and a sample incubated with chimeric peptide Tatp16 in HEK293 cell culture synchronized in G0/G1 phase after removal of synchronization block. FIG. 29B shows change in the number of cell in G2/M phase of the cell cycle in the same experiment. X-axis—incubation time (hours), Y-axis—abstract units.

Figure 30:
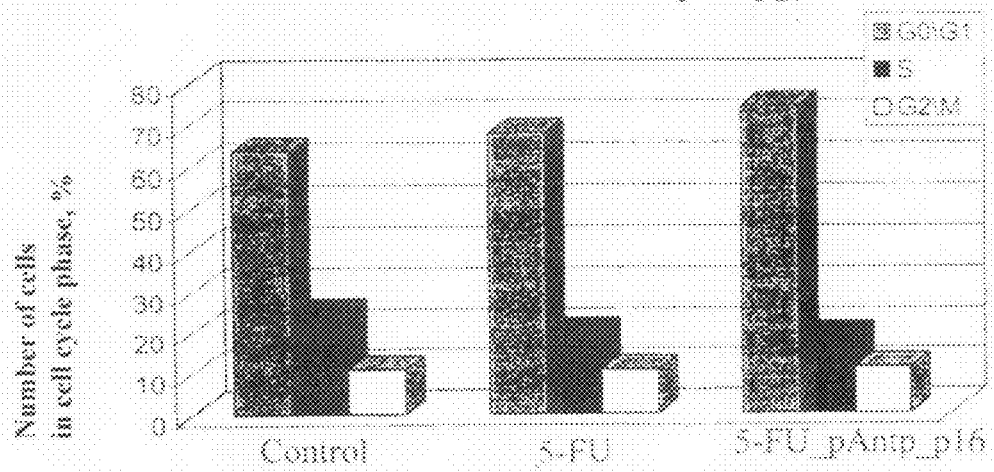
Figure 30:
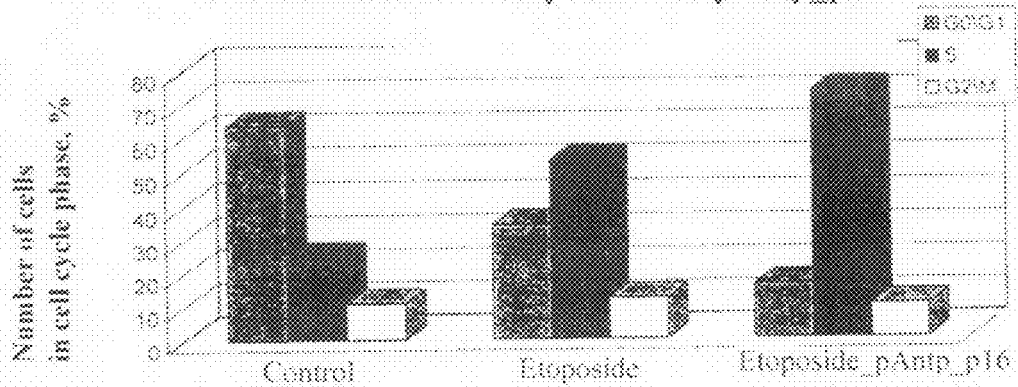
Figure 30:
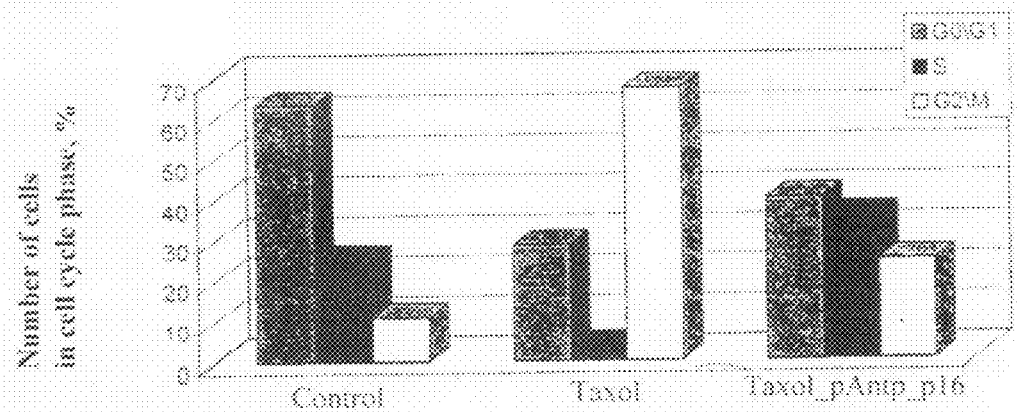

FIG. 30. Combined effect of chemotherapeutic agents 5-fluorouracil, etoposide and taxol at a concentration of 100 nMol and chimeric peptide pAntp p16 (2) at a concentration of 40 .mu.Mol. Cell cycle phase distribution in A549 cell culture after 24 hours of incubation with a chemotherapeutic agent and the peptide. Figure A—combined effect of 5-fluorouracil and chimeric peptide; Figure B—combined effect of etoposide and peptide pAntp_p16 (2); Figure C—combined effect of Taxol and chimeric peptide.

Figure 31:
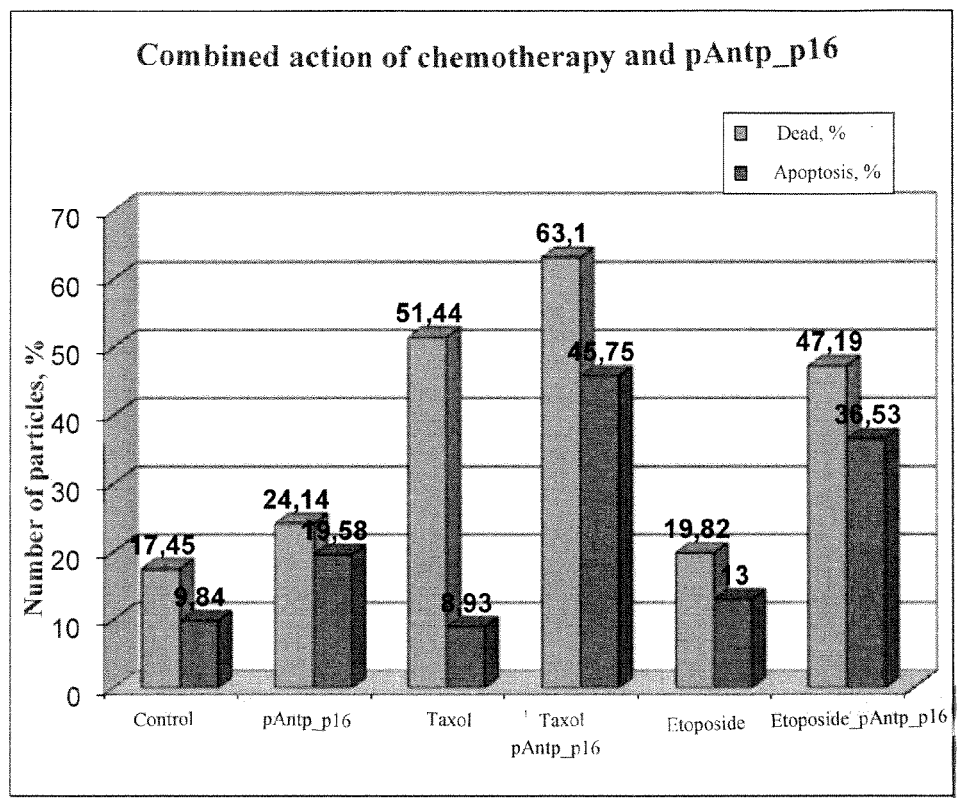

FIG. 31. Cytotoxic effects of chemotherapeutic agents taxol and etoposide at a concentration of 100 nMol and chimeric peptide pAntp_p16 (2) at a concentration of 40 .mu.Mol, combined effects. Y-axis—% of particles.

Figure 32:
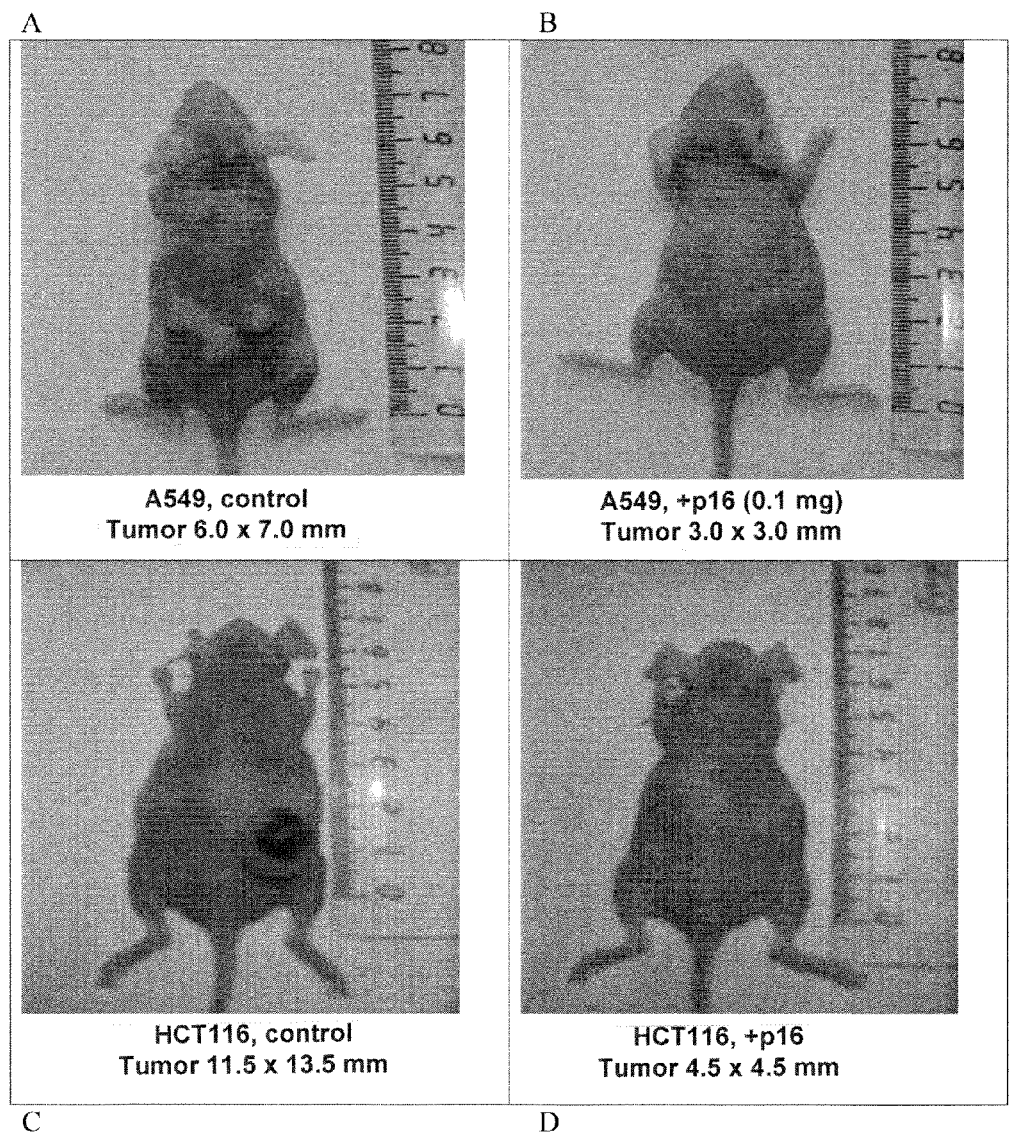

FIG. 32. Photographs of experimental animals at the time of 7.sup.th injection of the studied internalizable peptide p16_Antp. A and B—photographs of mice with A549 cells xenograft. A—mouse from a control group on day 16 of the experiment, tumor size is 6.0.times.7.0 mm. B—mouse from an experimental group on day 16 of the experiment after administration of p16 pAntp at a dose of 0.1 mg, tumor size is 3.0.times.3.0 mm. Figures C and D—mice with HCT-116 cells xenograft. C—mouse from a control group on day 18 after tumor cell transplantation (tumor size is 11.5.times.13.5 mm). D—mouse from an experimental group after seven p16_pAntp injections at a dose of 0.1 mg, tumor size is 4.5.times.4.5 mm.

Figure 33:
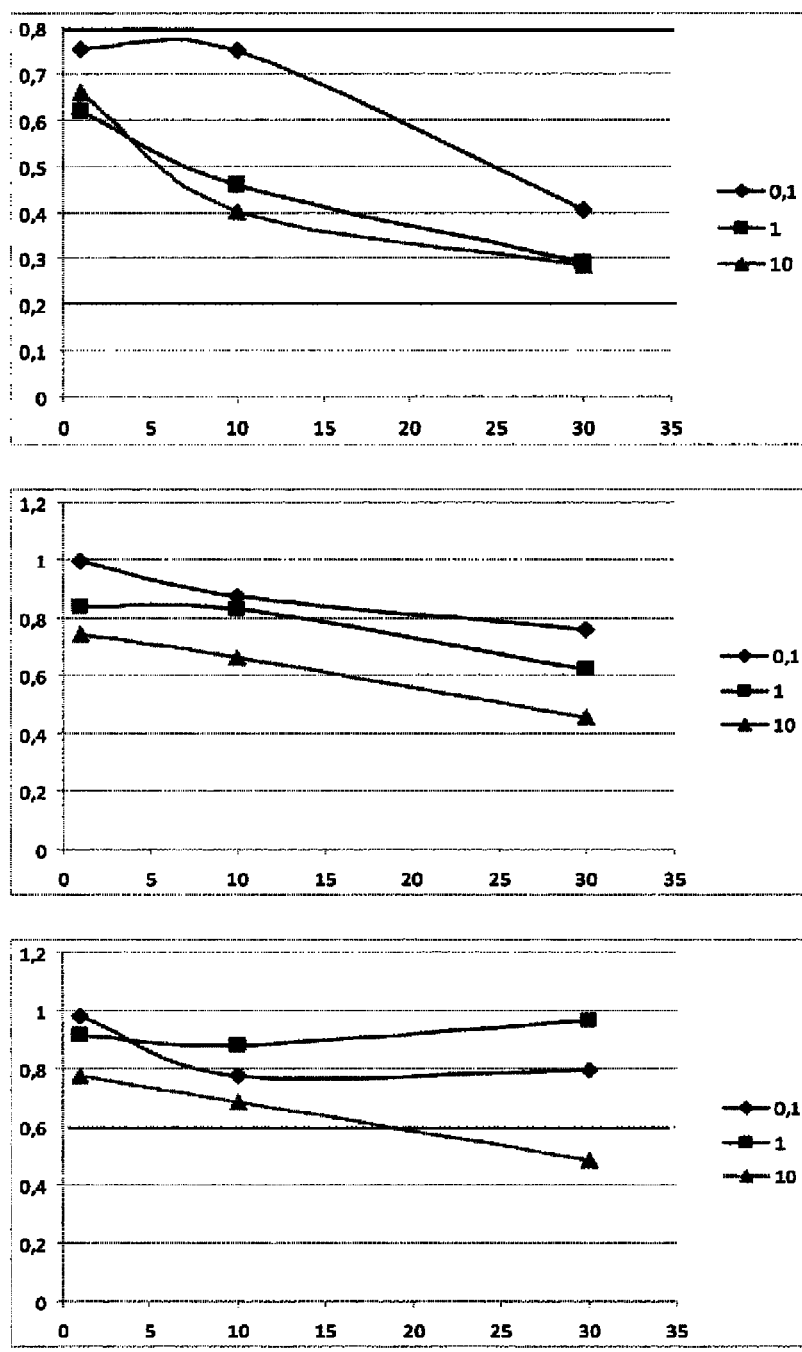

FIG. 33. Number of surviving cells (SBR3 breast cancer cell line) evaluated by MTT test. Each point is a mean of three wells. X-axis—concentration of chemotherapeutic agent. Upper graph—Taxol+peptide. Middle graph—etoposide+peptide. In each graph, three curves correspond to three of peptide concentrations. Concentrations of chemotherapeutic agents are 1, 10, 30 .mu.M. Peptide concentrations are 0.1, 1, 10 .mu.M.

Figure 34:
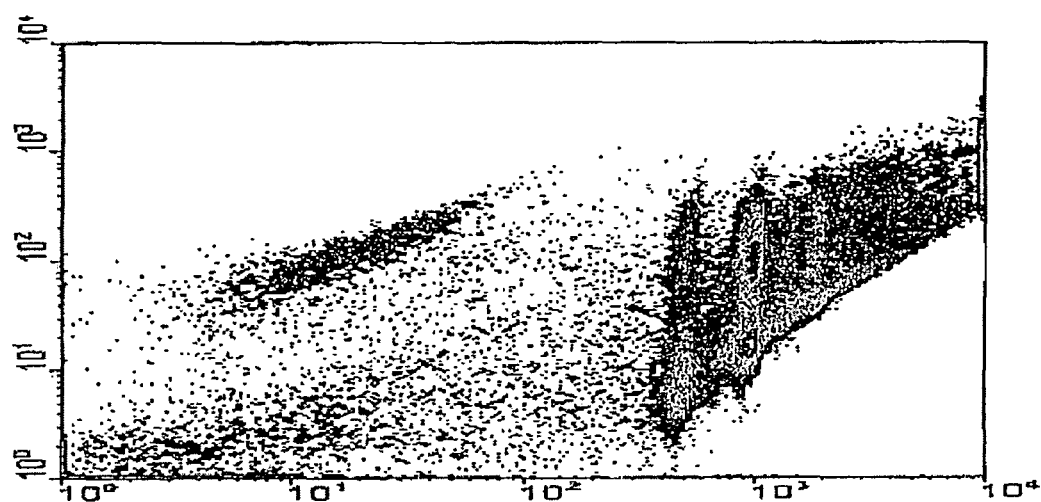

FIG. 34. Two-parameter cytogram of breast cells. X-axis—PI staining, Y-axis—cytokeratin staining Arrow indicated the region of "cytokeratin-positive apoptosis".

The following amino acid sequence listings are part of the disclosure of the present invention:

```
                                              SEQ ID NO: 1
DAAREGFLDTLVVLHRAGAR

SEQ ID NO: 2
RQIKIWFQNRRMKWKK

SEQ ID NO: 3
DAAREGFLDTLVVLHRAGARSRQIKIWFQNRRMKWKK
```

-continued

SEQ ID NO: 4
RGSDAAREGFLDTLVVLHRAGARRQIKIWFQNRRMKWKKSERKRGRQTYT
RYQTLELEKEFHFNRYLTRRRRIEIAHALCLTE

SEQ ID NO: 5
YGRKKRRQRRRG

SEQ ID NO: 6
PVKRRLDL

SEQ ID NO: 7
DAAREGFLDTLVVLHRAGARS YGRKKRRQRRRG

SEQ ID NO: 8
YGRKKRRQRRRGPVKRRLDL

The above enumerated sequence listings are also recorded on a compact disc, which contains a file named "Sequence_Listing.txt" created on Oct. 23, 2013 having a size of 5 KB.

PREFERRED EMBODIMENTS OF THE INVENTION

We studied the properties of six chimeric peptides containing different internalizable sequences and functional groups responsible for the inhibition of cyclin kinases. As internalizable vectors we used sequences of the proteins Antennapedia (pAntp, SEQ ID NO: 2) and internalizable sequence Tat (SEQ ID NO: 5). Antennapedia performs morphogenetic function of forming antenna in the fruit fly Drosophilia Melanogaster. Tat is a protein that performs a transactivator function in HIV virus causing AIDS. As functional groups we investigated a sequence of protein p16INK4a (SEQ ID NO: 1) which is a cyclin kinase inhibitor type D and the PVKRRLDL (SEQ ID NO: 6) sequence having high degree of homology with a functional fragment of cyclin kinase inhibitor p21. Most of the sequences were obtained by solid phase synthesis (see Table 3), one sequence is obtained by genetic engineering. This peptide is characterized by a longer fragment that has a transport function due to an insert of 44 amino acids of an Antennapedia protein, which according to the literature does not have any function. The need to increase the peptide sequence length is the result of practical constraints on the minimum size of proteins expressed in *E. coli*.

Since the alleged effect of intracellular peptides studied is the inhibition of cyclin kinase, we synthesized a control peptide (Antp_zam), containing an analogous sequence of protein p16INK4a (amino acids 82-102) with a substitution of tyrosine by alanine at position 92. This substitution was chosen because previous work by Ferouse et al. showed that substitutions at amino acid positions 91 or 92 result in the loss of inhibitory function of this peptide, characteristic for the p16INK4a sequence.

TABLE 1

Structure of the internalizable peptides studied.

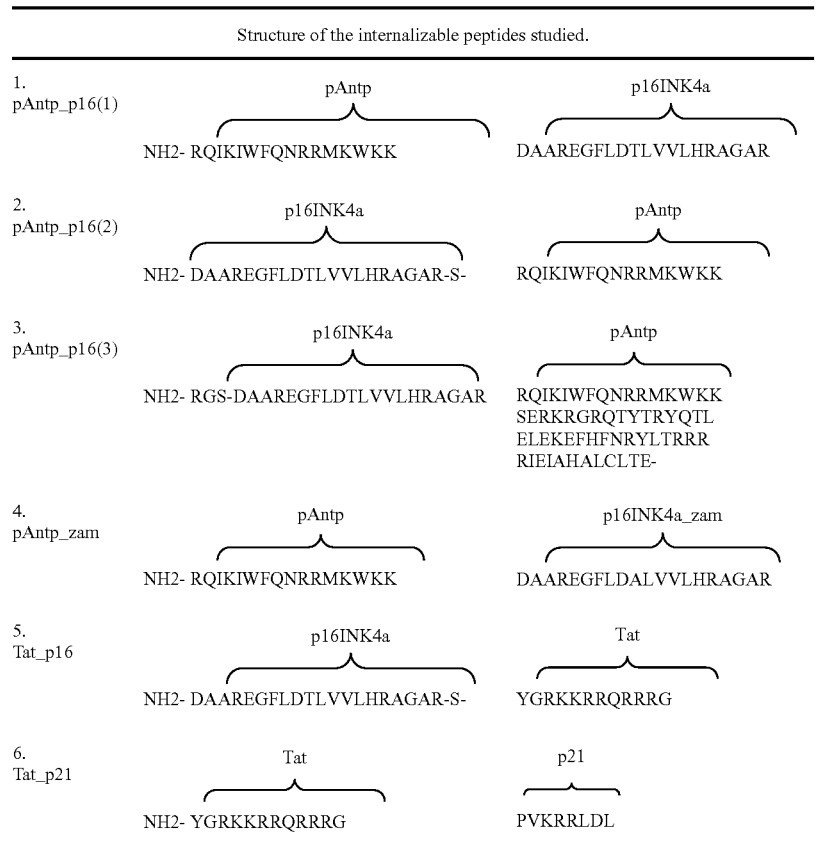

Peptides 1-3 are composed of a functional part p16INK4a (referred to SEQ ID NO. 1 attached hereto) and internalizable sequence pAntp (referred to SEQ ID NO. 2 attached hereto). The peptides are characterized by the location of the functional groups relative to the N- and C-termini of the molecule and by the presence of a peptide insertion in peptide 3 (prepared by genetic engineering). Peptide Antp_zam (4) comprises a sequence from p16INK4a protein (amino acids 82-102) with a substitution of tyrosine by alanine at position 92. This substitution was chosen because previous work by Ferouse et al. showed that substitutions at amino acid positions 91 or 92 result in the loss of inhibitory function characteristic for this sequence. Peptides 5 and 6 consist of internalizable Tat sequences (referred to SEQ ID NO. 5 attached hereto) and have different functional groups p16INK4a and p21Cip/Kip (referred to SEQ ID NO. 6 attached hereto).

One of the objectives of this invention was to study the influence of the position of the functional group and the peptide size on their biological activity. For this purpose three pAntp_p16 peptides (1-3, SEQ ID NO: 10, SEQ ID NO: 3, and SEQ ID NO: 4, respectively) were synthesized (Table 1). Peptides pAntp_p16 (1-2) (SEQ ID NO: 10 and SEQ ID NO: 3, respectively) are characterized by the location of the functional group p16INK4a (SEQ ID NO: 1): peptide 1-p16INK4a is located at the C-terminus of the molecule (SEQ ID NO: 10), peptide 2-p16INK4a is located at the N-terminus (referred to as SEQ ID NO. 3 attached hereto), peptides are obtained by solid phase synthesis. In the chimeric peptide pAntp_p16 (3) (referred to as SEQ ID NO. 4 attached hereto) which is produced by genetic engineering, the functional group p16INK4a (SEQ ID NO: 1) is located at the N-terminus but has an insert of 44 amino acids. In addition, the study included p16.sup.+ and p16.sup.− cell cultures. p16 and p53 gene expression in cell lines used is indicated in Table 2. The cytotoxic effect was independent on p16 expression.

TABLE 2

| | Cell line | | | | |
|---|---|---|---|---|---|
| Gene | Jurkat | Raji | A549 | MCF7 | HEK293 |
| p16 | − | + | − | − | + |
| p53 | wt, poorly expressed | + | +, wt | +, wt | + |

Example 1

Study of penetrating ability of internalizable peptides. To register the penetration of peptides into the cell and to study the dynamics of accumulation we used identical chimeric sequences conjugated to a fluorescent label fluorescein isothiocyanate (FITC). Since the inclusion of FITC molecules into a polypeptide product often leads to a substantial change in its physical-chemical properties and loss of physiological activity, a lysine molecule was added to the original sequence at the N terminus which carried a single FITC molecule.

The method of fluorescent light microscopy showed that the studied peptides bind to cells and penetrate the cell lines Raji, Jurkatt, A549 HEK 293 and human peripheral blood lymphocytes. By flow cytometry we showed the binding of peptides to cells and the absence of the effect of fluorescence quenching by trypan blue which indicated the accumulation of peptide within the cell.

Figure 1:
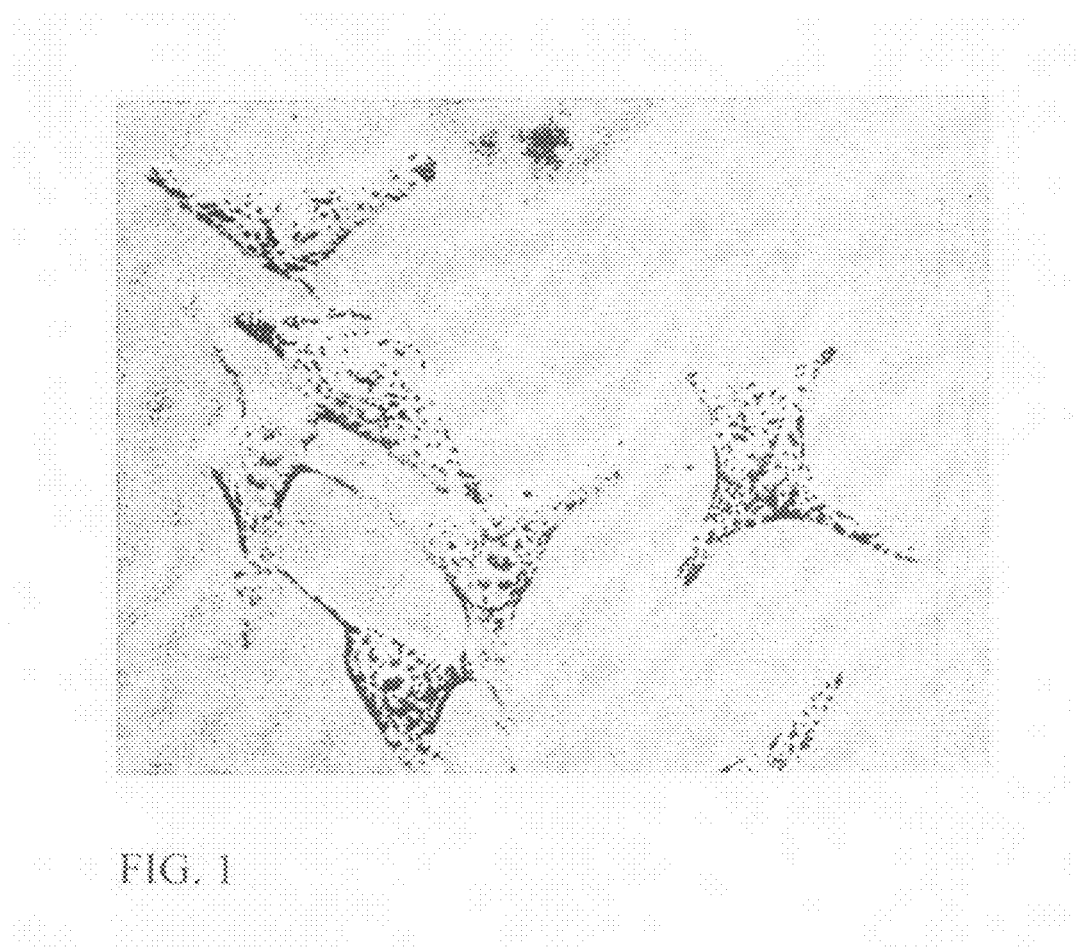
FIG. 1. Scan of cell line A549 which was incubated for 15 min with the peptide, using a laser scanning microscope Leica TCS SP2 (provided by the Odessa State Medical University). The figure shows cells in which the chimeric peptide pAntp-p16-FITC is visible as light spots.

The most objective data on peptide accumulation within the cells were obtained using the method of laser scanning microscopy (FIG. 1). Protein labeled with fluorescein isothiocyanate was dissolved in 0.9% NaCl. A549, HEK293 cell lines were grown on sterile slides and placed in a special chamber directly under microscope eyepieces. The medium was then replaced by the one with a test protein. Saturation with the protein was observed over time. In addition, we performed layer by layer scan of cells in order to determine the localization of the peptide.

Figure 2:
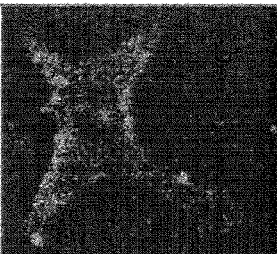
FIG. 2. Distribution of protein pAntp_p16 in A549 cells as function of time. 1, 15 and 30 minutes after the addition of protein. Leica Laser Scanning Microscope.

Analysis of the images obtained with this magnification did not reveal any pre-emptive localization of the pAntp-p16 protein in the cell. Obviously, the protein is distributed uniformly in the cell compartments. The penetration of the protein into the cell is quick enough. As soon as 15 minutes of incubation its relatively homogeneous distribution in the intracellular space can be observed (FIG. 2).

The rate of peptide penetration in human peripheral blood lymphocytes and lymphocyte cell lines (Raji, Jurkatt) was estimated using the method of flow cytometry. This method allows us to investigate a large concentration of cells over time and is convenient for the estimation of the rate of penetration of a test peptide. We measured the fluorescence of lymphocytes under the influence of protein p16-pAntp-FITC at pH 7.5 and pH 6.0. The principle of the method is based on a lower FITC fluorescence quantum yield in solutions with a more acidic pH. Since the measurement speed is fast enough, the pH inside the cell cannot change. Lymphocytes were incubated with a peptide for 1-15 minutes, then 20-fold volume of phosphate buffer of pH 6.0 and pH 7.5 was immediately added thereto. Thereby we estimated the difference in fluorescence intensity. In the majority of measurements, fluorescence intensity did not significantly change after 15 minutes of incubation. Thus, it can be assumed that after 15 minutes incubation the peptide completely penetrates within the cell.

To study the rate of accumulation of a peptide inside the cell we used the flow cytometry method. For this purpose, a FITC-labeled peptide was injected directly into the flow cytometer measuring tube, allowing us to register the dynamics of cell fluorescence. We investigated mononuclear fraction of blood leukocytes from healthy donors, isolated on Ficoll gradient.

We could see that after a short lag phase, there was a rapid accumulation of the peptide in the cells of normal lymphocytes. The final concentration is reached in a time equal to .about.1 min.

Figure 3:
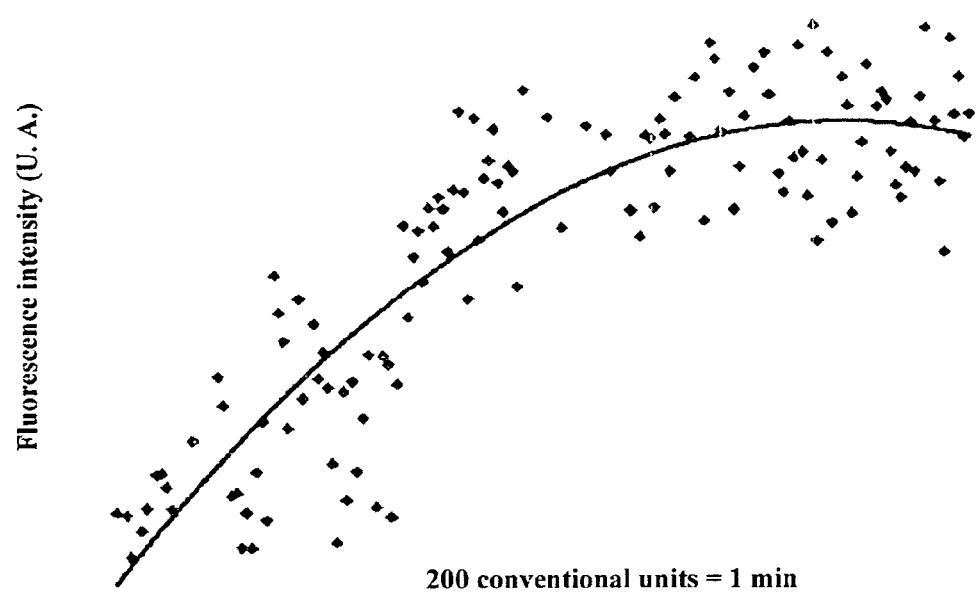
FIG. 3. Kinetics of accumulation of FITC-labeled peptide p16pAntp in peripheral blood lymphocytes in vitro. X-axis-time in abstract units (U.A.), Y-axis—fluorescence intensity (U.A.).

FIG. 3 shows only a fragment of the curve reflecting the kinetics of accumulation of a chimeric protein in the cell.

This kinetics curve is best described by a power function of the type C=const 1-const 2*t.sup.2+const 3, reflecting the regression coefficient (=0.79).

Figure 4:
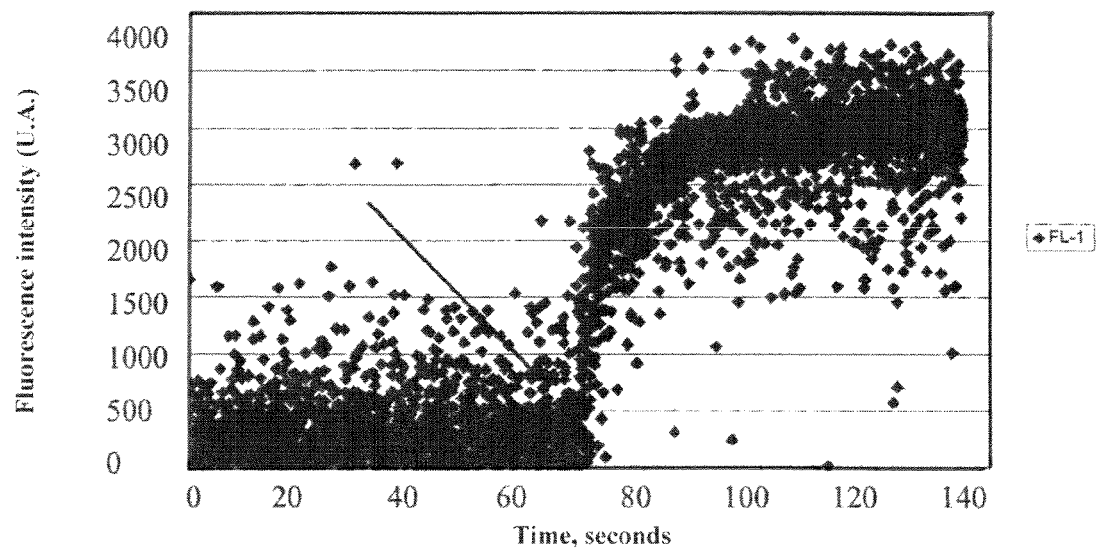
FIG. 4. Dynamics of accumulation of FITC-labeled chimeric peptide pAntp_p16 in a Jurkat cell line. Arrow indicates the addition of the chimeric peptide to the flow cytometer vat.

Similar kinetics of peptide accumulation was obtained for cells of malignant lymphomas. As models we studied cell lines Jurkat (derived from lymphoblastic leukemia and having a T-cell phenotype) and Raji originating from Burkitt's B-cell lymphoma. FIG. 4 shows dynamics of FITC-labeled peptide accumulation in Jurkat cells.

The above graph shows that the peptide penetrates in tumor cells at high rate as well. The time to maximum concentration is less than 1 min. The kinetics of accumulation was investigated at room temperature (t=20.degree. C.). It should be emphasized that the mechanism of the penetration for the studied class of peptides is not known hitherto. However, it has been shown that the accumulation is equally effective even at +5.degree. C. It is not related to energy expense in the cell, not mediated by cellular receptors and it does not use the phagocytosis and pinocytosis pathways. We also confirmed the fact of accumulation of the synthesized peptide containing internalizable fragment at different temperatures (up to +5.degree. C.).

Figure 5:
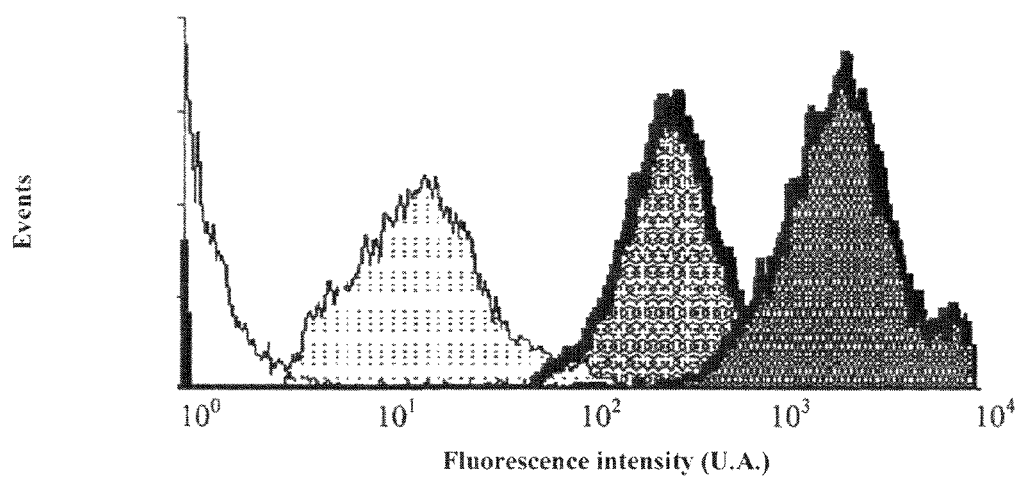
FIG. 5. Fluorescence intensity and intracellular concentration of the drug in medium. The first peak represents the fluorescence intensity upon addition of FITC-labeled Antp_p16 chimeric peptide at a concentration of 0.1 .mu.Mol to a Raji cell culture, incubation with the peptide 15 minutes in the dark; the second and third peaks represent a change of intracellular fluorescence intensity when the extracellular peptides concentration is changed by 1 and 10 .mu.Mol, respectively.
Figure 6:
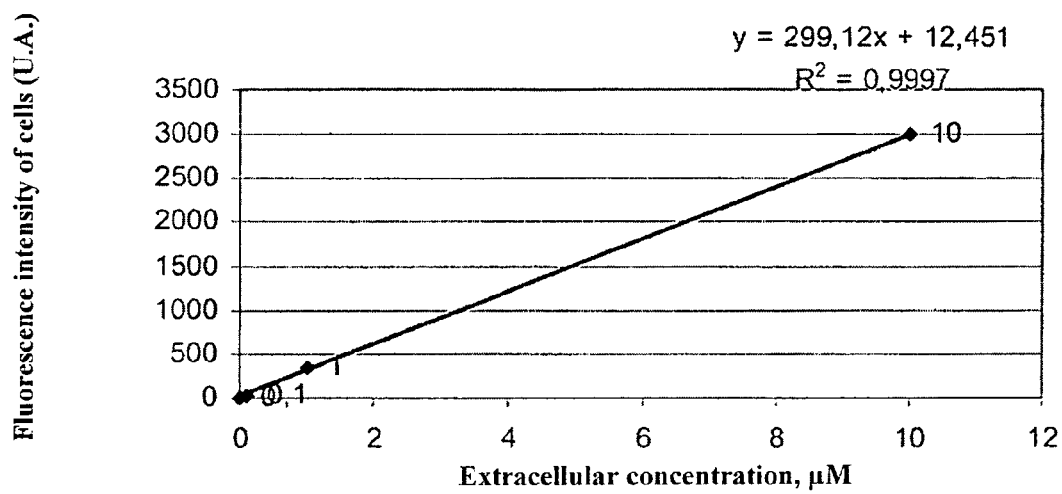
FIG. 6. Dependence of fluorescence intensity of cells on extracellular concentration of chimeric peptide.

We also investigated the dependence of the amount of peptide accumulated in the cells on its extracellular concentration. FIGS. 5 and 6 show the variation of cell fluorescence intensity depending on the extracellular concentration.

FIG. 6 shows the same data, illustrating the fact that the ratio of extra- to intracellular concentration is linear (in the investigated concentration range). Since investigated peptides can cross the cell membrane in both directions, it can be assumed that the accumulated cell peptides can leave the cell with a decrease in the extracellular concentration. Investigation of the processes of peptide export from the cell may be a subject of separate studies.

Thus, as a result of the experiments, it was shown that the kinetics of accumulation of a chimeric peptide containing an internalizable fragment and a protein p16INKa fragment (SEQ ID NO: 1) has a power dependence of the type $C=const1+const2*t^2$. It is also shown that the dynamics of accumulation and intracellular distribution of the peptide in normal and tumor cells does not differ in the nature and rate of accumulation.

Example 2

Comparative Evaluation of the Functional Activity of the Peptides Comprising the Active Centers p16INK4a and p21/CIP/KIP One of the basic conditions for the construction of chimeric peptides based on protein inhibitors of cyclin kinases was the presence of proven inhibitory properties of specific peptide fragments. Therefore, in the work we compared fragments of the proteins p16INK4a (SEQ ID NO: 1) and p21/CIP/KIP (SEQ ID NO: 6) for which such sequences are described.

The gene products p16 and p21 are inhibitors of complex formation between cyclin and cyclin-dependent kinase and, therefore, are the regulators of the cell cycle. Therefore, the study of the function of exogenous chimeric peptides with functional groups p16 and p21 was focused on the study of the proliferative activity and the study of the level of apoptosis in cultures upon incubation with internalized peptides.

Figure 7:
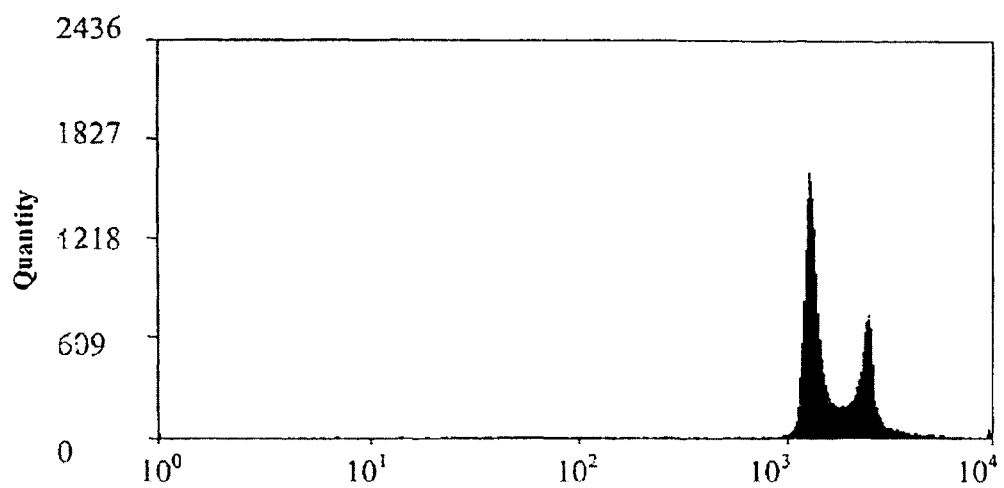
FIG. 7. Example of DNA histograms obtained by flow cytofluorometry. X-axis—fluorescence intensity, Y-axis—number of cells. Particles in the area before the location of diploid cells (pre-diploid peak) are fragments of apoptotic cells. Their number is proportional to the level of apoptosis in the test cell population. A—control A549 cells; B—cells treated with pAntp-p16 (40 .mu.M). 24 hours incubation.
Figure 7:
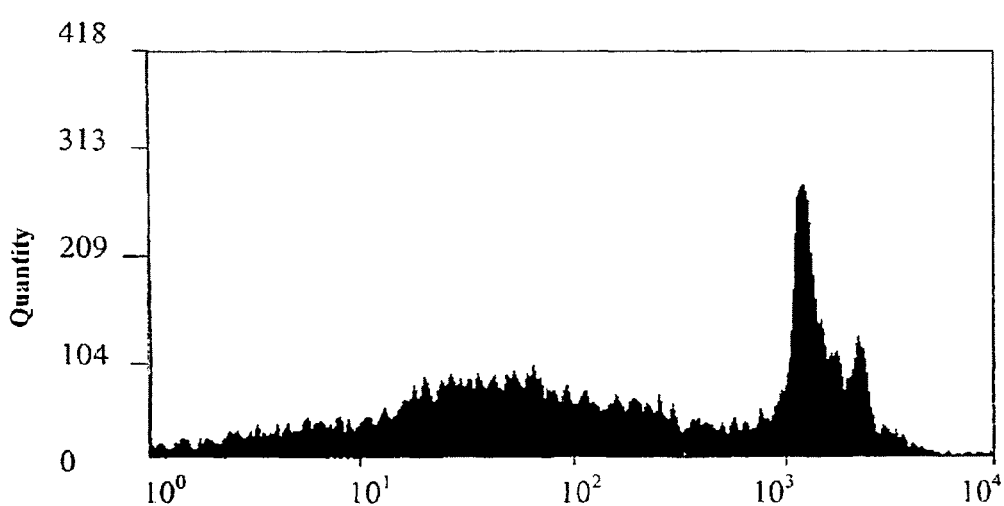
Figure 8:
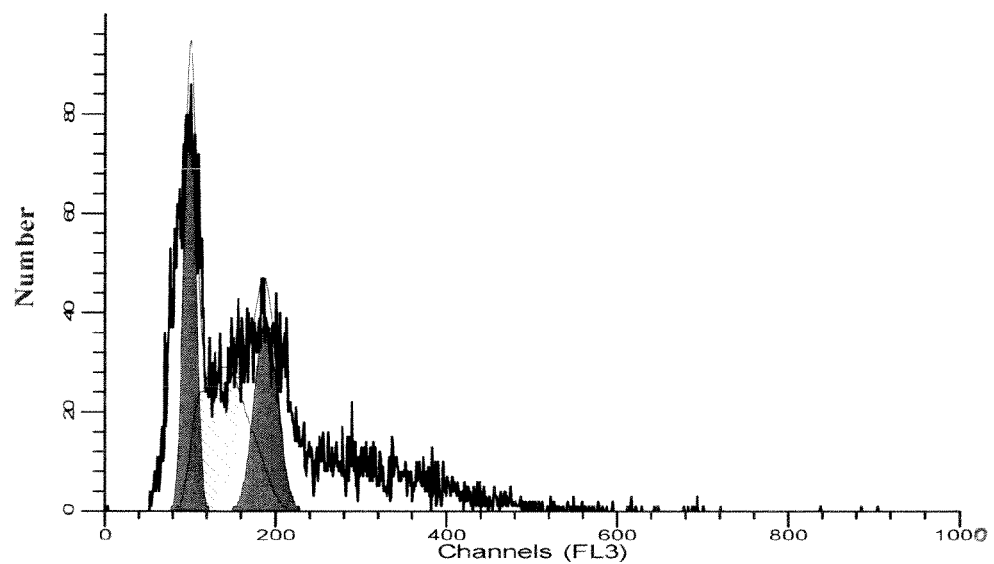
FIG. 8. Example of DNA histograms obtained by flow cytofluorometry using the ModFit LT 3.0 software; A—control cells, A549, B—cells treated with pAntp-p16 (5 .mu.M). The figure shows cell cycle phases G0/G1, S, G2/M. According to the area occupied by a peak phase the software program Modfit LT 3.0 calculates a relative number of cells in the phase.
Figure 8:
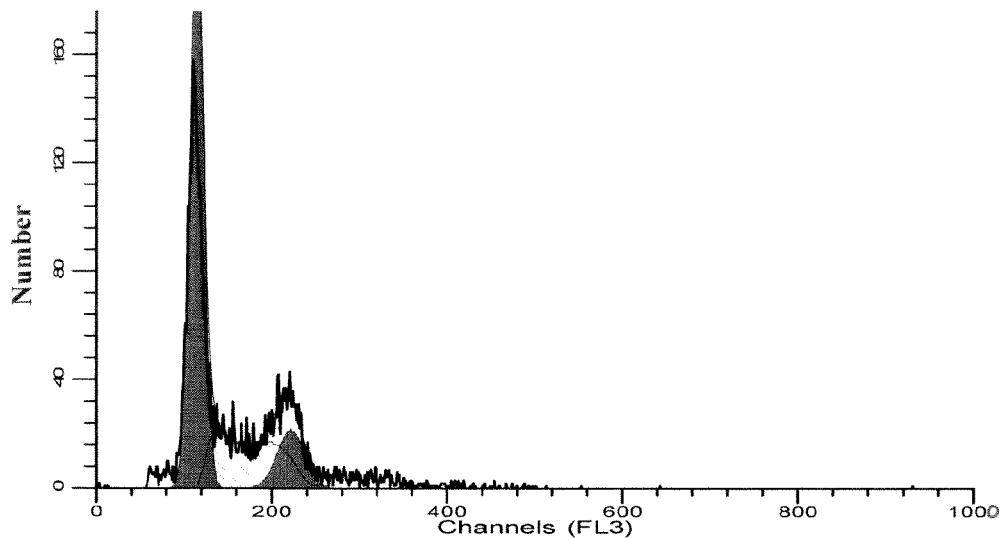

In experiments with cell lines we evaluated the distribution of cells according to the phases of the cell cycle and calculated the proliferation index. For analysis we used software FloMax 2.0 (built-in option of flow cytofluorimeter) and software Modfit LT 3.0 (FIGS. 7 and 8). We also carried out the determination of the proportion of cells entered the apoptosis based on size of "pre-G1-hypodiploid" peak on DNA histogram (FIG. 8 (B)). Experiments were performed both on cell lines synchronized in phase G1/S, and on non-synchronized cell lines Raji, Jurkatt, A549, HEK 293, MCF-7.

Figure 9:
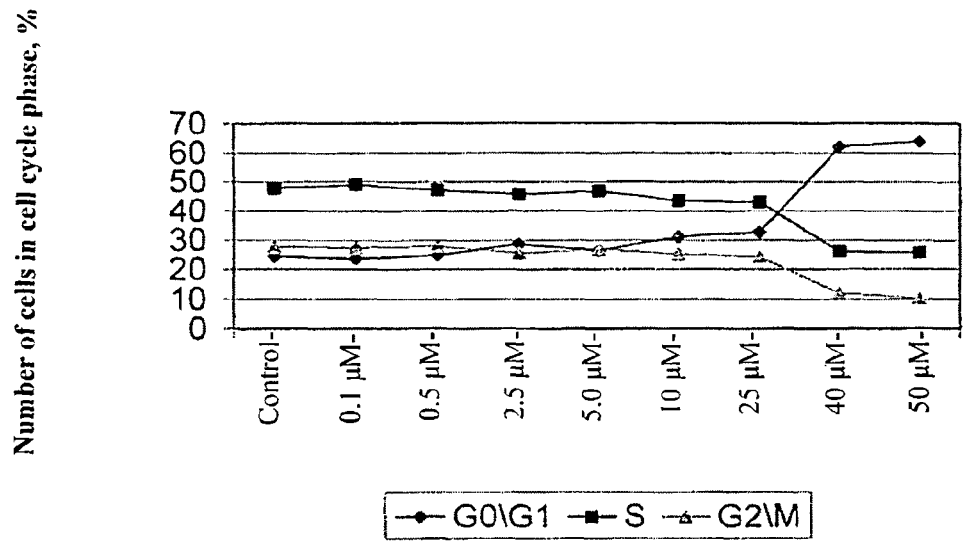
FIG. 9. Dependence of average values of cell cycle phases on peptide concentrations. A—internalized peptides with the active center p16INK4a, B—internalized peptides with the active center p21. At concentration of peptides of 40 .mu.Mol a change in the proportion of cell cycle phases which was significantly different from the control sample.
Figure 9:
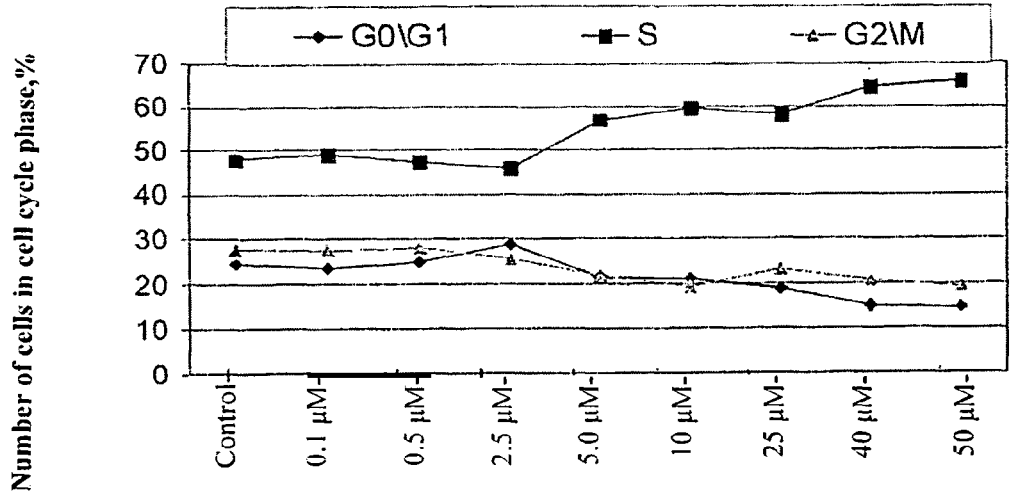

Several preliminary experiments involving all investigated peptide sequences set the optimal concentration of the peptides that reaches 100 .mu.M (FIG. 10), suggesting a possible drug concentration of about 400 mg/kg. However, stable antiproliferative effect is observed already at a concentration of 40 .mu.M in all cell lines examined, which does not change significantly with increasing concentrations of the drug (FIG. 9). The number of viable cells does not decrease below 50%. The number of apoptotic particles at a given concentration and the incubation time of 24 hours is about 40% and increases to 60% when increasing the concentration up to 50 .mu.M (FIG. 10).

Figure 10:
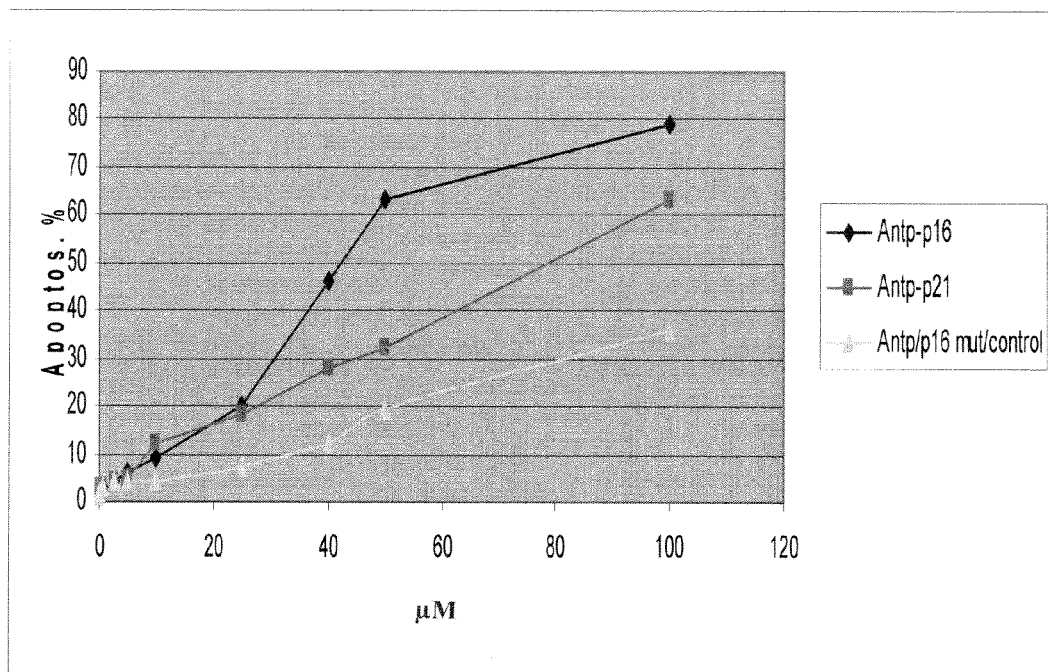
FIG. 10. Dependence of average level of apoptosis on concentrations of the peptides. At concentration of the studied chimeric peptides the level of apoptosis was significantly different from controls.
Figure 11:
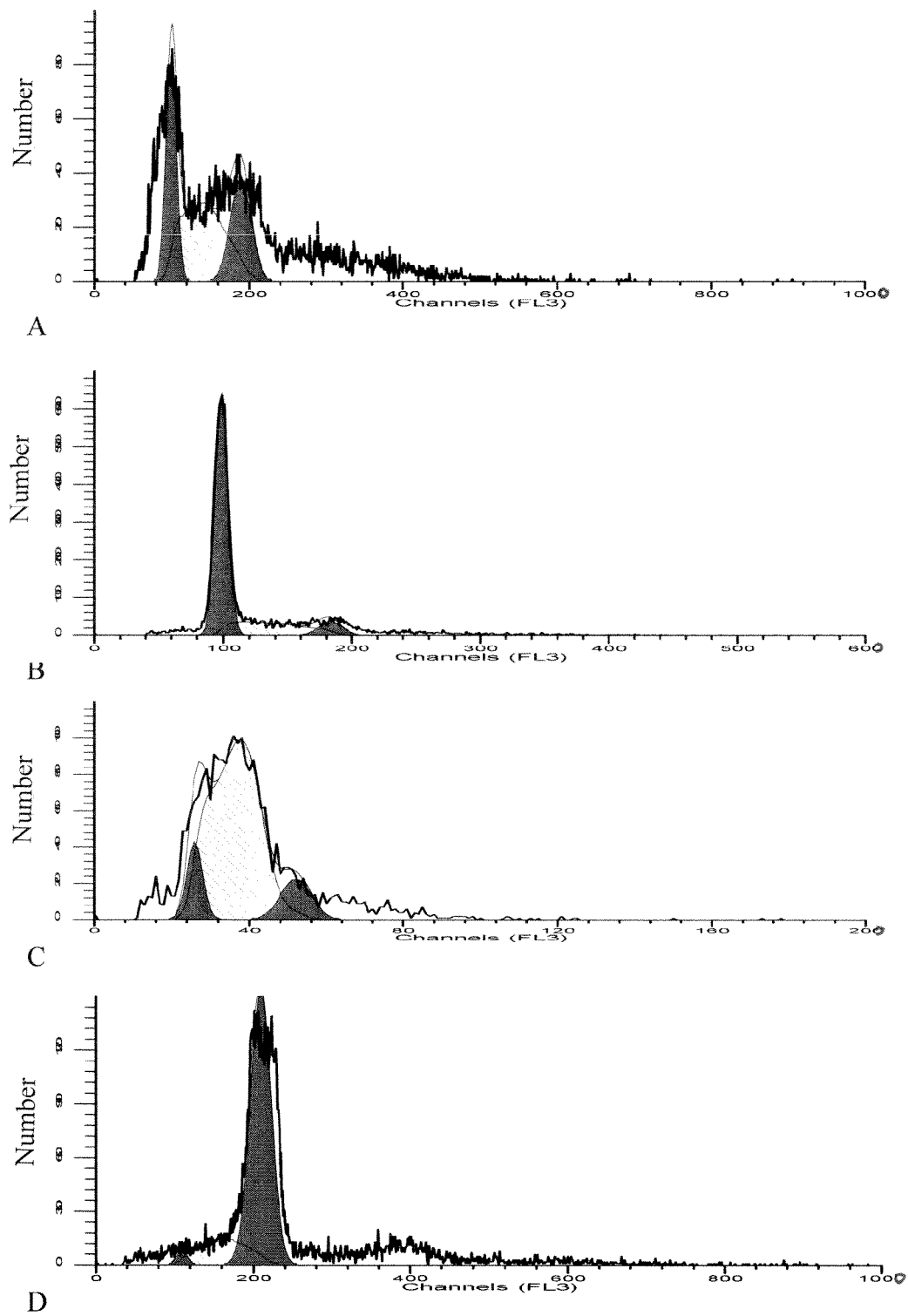
FIG. 11. Synchronization of cell cultures. Figure A—cell cycle phase distribution of unsynchronized cell culture; B—synchronization in G0/G1 phase by depleted medium method; C—synchronization in S phase by double thymidine block technique; D—synchronization in G2\M—phase by incubation with Taxol.

FIGS. 10 and 11 show that anti-proliferative and cytotoxic effects are concentration dependent. At low concentrations, up to 5 .mu.M the effect of the drug is very low, although as mentioned above, the peptide is able to penetrate the cells at extracellular concentration of 0.1 .mu.M.

Thus, the selected concentration was equal to 40 which satisfies the above requirements and would be adequate for all the investigated peptides.

The study of the effects of peptides was conducted on transplantable cell cultures. In order to study alterations in the expression of specific intracellular regulators and in order to improve visualization of the experiments, the cells were pre-synchronized.

Depending on the method of synchronization the cell cultures are trapped in the G0/G1, S and G2/M-phase of the cell cycle (FIG. 11).

Figure 12:
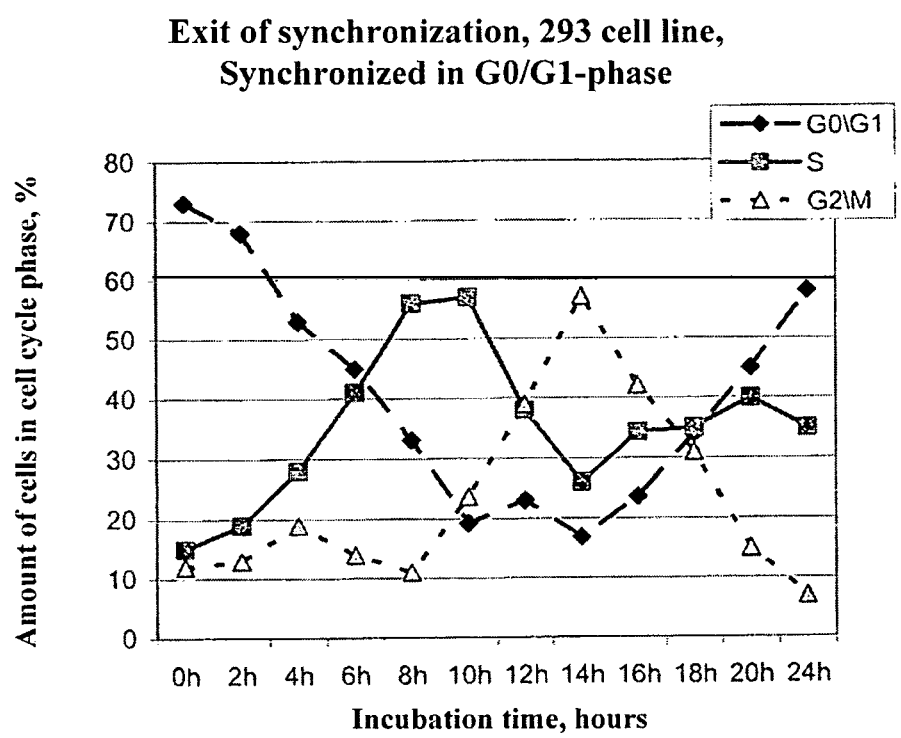
FIG. 12. Falling out of synchronization and change of the percentage of cells in different phases of the cell cycle for the HEK293 cell line synchronized in G0/G1 phase.

FIG. 12 shows how the distribution of the cells in different phases of the cell cycle is changed following withdrawal of the sync block in the culture synchronized in G0\G1-phase. At time 0 (time of removal of a sync block) most cells were in phase G0\G1 (73%) and in phases S and G2\M-15% and 8%, respectively, then we can observe decrease in G0\G1 phase with simultaneous growth of S-phase, after a certain period of time the percentage of cells in G2\M-phase begins to increase. The character of exit out of sync block is typical for all investigated cell cultures, it should also be noted that the doubling time of all test cell was about 24 hours.

Example 3

Evaluation of Antiproliferative Activity of Chimeric Peptides with Different Active Centers At the first stage of the evaluation of the obtained results, we investigated the effect of internalizable chimeric peptides with different active centers—p16INK4a and p21/CIP/KIP. The chimeric peptide to be studied was added at the moment of the sync block removal. Cell cycle analysis was performed every 2 hours for 24 hours after removal of the block.

Figure 13:
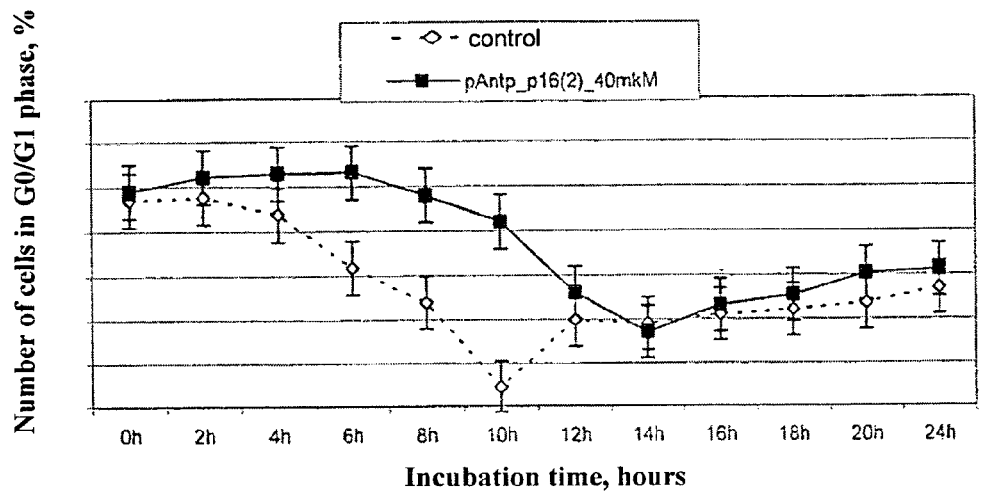
FIG. 13. Effect of chimeric peptides comprising a p 16INK4a fragment on cell cycle in synchronized cell culture of HEK293 cells. A—change of cell number in G0/G1 phase, B—change of cell number in S phase of the cell cycle. X-axis—incubation time, hours; Y-axis—number of cells in a defined cell cycle phase, %.
Figure 13:
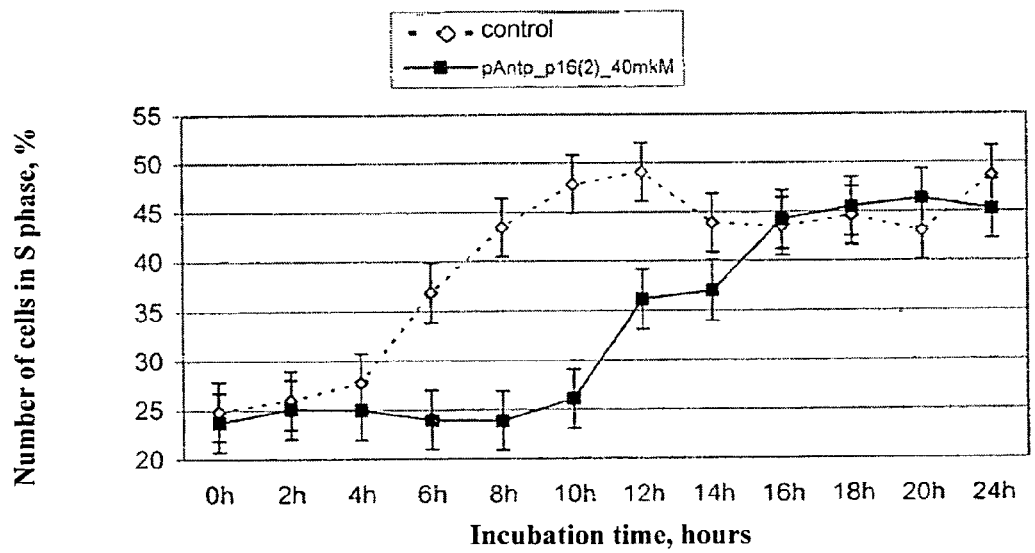

In the study of antiproliferative activity of these peptides we established that the peptides with the p16INK4a active center causes arrest of the cells in G0/G1 phase of the cell cycle (FIG. 13). This effect is more clearly visible in the cell culture synchronized in the G0-phase using the method of synchronization by medium depletion. It is registered only during the first cell division after removal of the sync block.

FIG. 13 shows that in the control (cells synchronized without addition of the chimeric peptide), increased S-phase is observed 4 hours after withdrawal of sync factor, and the reduced G0/G1-phase is observed. After addition of the chimeric peptides with the p16 active center the reduction of G0/G1 and S growth occurs later than in the control, G0/G1 starts to decrease 6 hours of after incubation, and visible growth of S-phase can be observed 8 hours after incubation.

In the study of a chimeric peptide p21/CIP/KIP (FIG. 14), it was found that changes of G0/G1-phase in control sample are not different from those of the sample with the peptide, however, high levels of S-phase in the test sample (65-70%) remains over 14 hours of incubation, whereas the level of S-phase in the control sample already starts to decrease after 10 hours of incubation and at 14 hours of incubation is on average 45%. The G2/M-phase level in the peptide sample reaches a maximum value after an average of 18-20 hours of incubation and after 10-12 hours in the control sample. Thus, one can conclude that the main antiproliferative effect of peptide with the active center p21/CIP/KIP is the arrest of transition of cells from S-phase in G2/M-phase (FIG. 14).

As in the case of a chimeric peptide comprising p16INK4a fragment, in order to better illustrate the effect induced by Tat_p21 peptide, we selected synchronization in G0-phase with the reduced medium.

Figure 14:
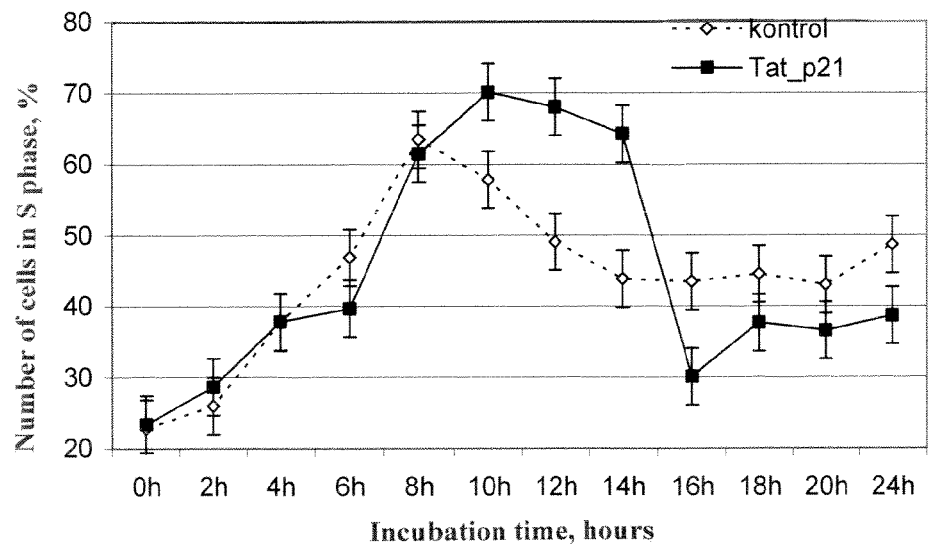
FIG. 14. Effect of a chimeric peptide comprising a p21 fragment and the internalizable Tat sequence on cell cycle in synchronized HEK293 cell culture. A—change of cell number in S phase of the cell cycle. B—change in cell number in G2/M phase of the cell cycle. X-axis—incubation time, hours; Y-axis—number of cells in a defined cell cycle phase, %.
Figure 14:
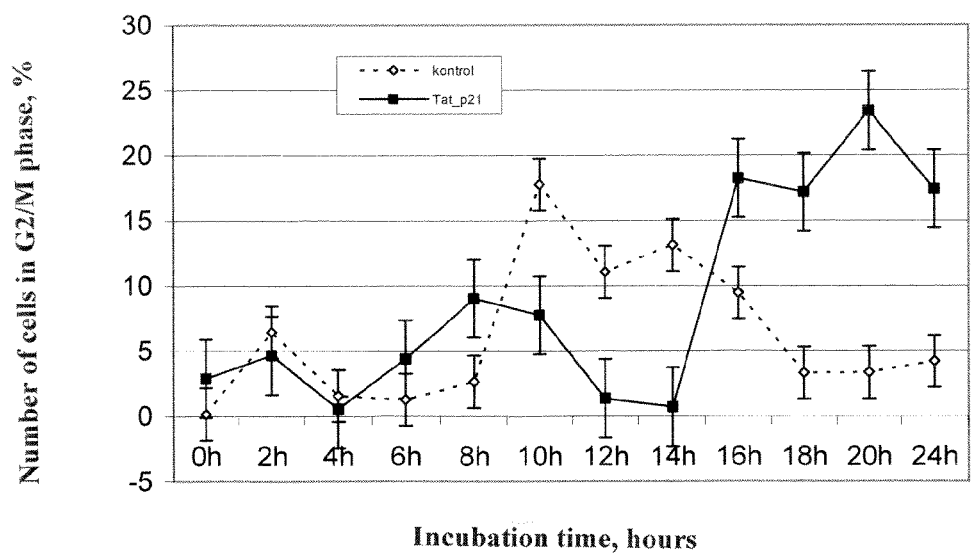
Figure 15:
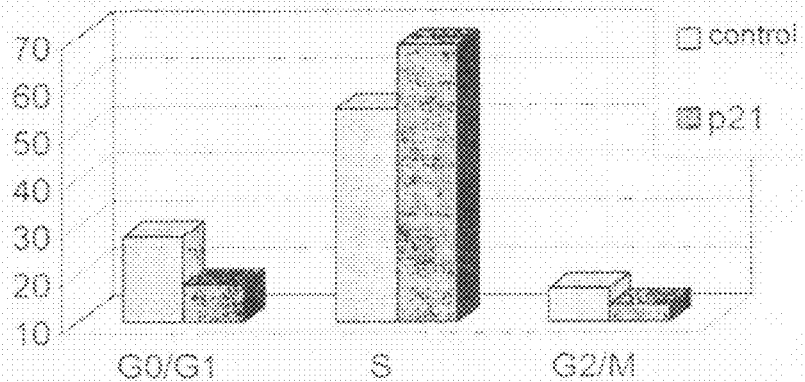
FIG. 15. Distribution of cell cycle phases for synchronized HEK293 cell line after addition of chimeric peptides with p21
Figure 15:
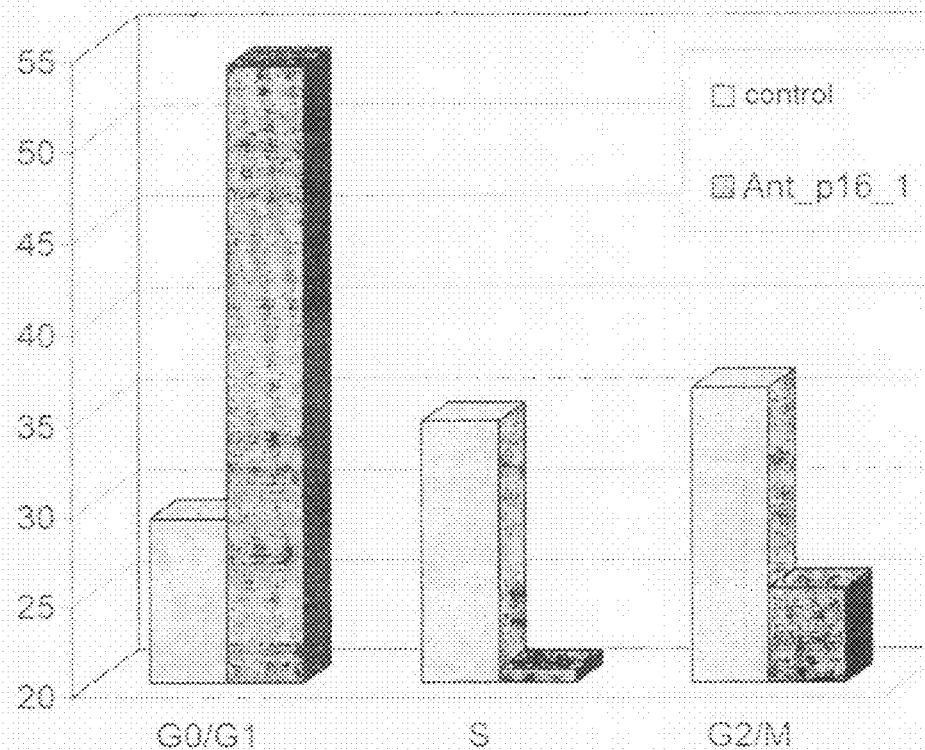

As seen from FIGS. 13 and 14, at a certain time point we can determine maximum difference between the phases of the cell cycle in control and experimental samples. For the test peptides, the maximum difference time was 8-12 hours after the removal of the sync block. Given that the accumulation of the peptide within the cell occurs within the first few minutes after addition of the peptide into the extracellular medium, it is possible to assume that the observed effect is due to the impact point of the active center of the chimeric peptide on the host cell genome. For the peptides with p16 active center the maximal differences were observed at 8-10 hours of incubation and for the peptide with p21 active center at 10-12 hours (FIG. 15). Probably, this small difference is due to the fact that, as discussed above, p16 causes an arrest of the G1-S transition, and p21 arrests the S-G2/M transition.

Example 4

Study of Influence of Chimeric Peptide Comprising Functional Groups p16INK4a and p21/CIP/KIP on the Level of Apoptosis One of the major trends in the development of anticancer drugs is to search for drugs that can selectively induce apoptosis in tumor cells. Apoptosis is a genetically controlled process. A large number of works shows the relationship of cell transition into apoptosis with the inability to overcome one of the control points (checkpoints) during the passage of cell proliferation phases.

We showed that the investigated chimeric peptides are capable of activating apoptosis in various cell lines (FIG. 16).

While investigating the differences of the cytotoxic effect depending on the structure of the active site we found that the chimeric peptides comprising the functional sequence of the protein p16INK4a have a more pronounced cytotoxic effect compared with peptides comprising the sequence of p21/CIP/KIP. When comparing the mean values of apoptosis for Tat_p21 (referred to SEQ ID NO. 8 attached hereto) peptides and pAntp_p16 peptides together with Tat_p16 (referred to SEQ ID NO. 7 attached hereto), it was found that there are no significant differences between the control samples and samples with Tat_p21 peptide (FIG. 16).

Analyzing the level of apoptosis depending on the time of incubation with a peptide, for peptides with p16INK4a active center, we established the dependence of the level of apoptosis from the incubation time. In case of chimeric peptide with p21 fragment, this dependence has not been observed. As is seen from FIG. 17, the level of apoptosis in the study of peptides including p16 fragment has a maximum which is located at 8-10 hours of incubation and thus coincides with the arrest in G1-S transition caused by it.

Example 5

Study of the Effect of the Peptide Vector Structure on Examples of Tat and pAntp We studied two types of peptide transporters, Tat and pAntp. The structure and characteristics of these vectors is discussed in the background section.

We investigated chimeric peptides having p16INK4a active center and having different types of vectors, Tat and pAntp. While investigating the influence of the vector type on processes of cell proliferation, it was found that the investigated Tat_p16 and pAntp_p16 affect the same cell cycle phases, causing an arrest of G1-S transition. As is seen from FIG. 18, plots of dependencies of the number of cells in the cell cycle phases are similar in appearance for the two types of peptide vectors carrying p16 fragment. In the control sample—synchronized cell culture without the addition of the study peptide, the number of cells in G0/G1-phase starts to decline as early as 2 hours after removal of the synch block, and 10 hours later we recorded the lowest number of cells in G0/G1-phase. S-phase in the control samples starts to increase 4-6 hours after sync block removal and reaches a maximum after 12 hours. In samples with chimeric peptides, as is seen from FIG. 18, there is a G0/G1-phase arrest.

Thus, when incubated with pAntp_p16 peptides, G0/G1 phase level begins to decrease 6-8 hours after incubation, and reaching the lowest level after 14 hours, whereas the level of S-phase begins to increase 10 hours after incubation. In the case of chimeric peptide Tat_p16, there is no clear transition in increase of S phase and decrease in G0/G1-phase. G0/G1 begins to decrease simultaneously with G0/G1-phase in control sample, however, its level decreases more slowly than in the controls. S-phase in the sample with Tat_p16 test peptide begins to increase 12 hours after incubation and has a maximum after 14 hours incubation with peptide. In control samples, a maximum S-phase is detected 12 hours after the removal of a sync block.

PAntp_p16 and Tat_p16 induces the same delay of the cell proliferation, the maximum difference in the control and test samples corresponds to about 12 hours of incubation (FIG. 19). This time interval in the control group reflects the G1-S transition. Thus, we can assume that in the case of chimeric peptides with the p16INK4a active center, the vector structure does not affect the antiproliferative effect of peptide.

When evaluating the effect of the peptide vector structure on cytotoxic effect we observed that in the case of the pAntp_p16 chimeric peptide, the level of apoptosis in the sample is higher than for the incubation with Tat_p16 peptide (FIG. 20). Apoptosis inducible by addition of the chimeric peptide to the culture depends on cell lines and on apoptosis in the control sample. In the cell lines A549 and MCF-7, the level of apoptosis in the control samples is at the 5% level, while incubation with the chimeric peptide pAntp_p16 increased it to an average of 25%. In the control samples of Raji, Jurkat lines, the level of apoptosis was 12% while in the samples with the peptide it was 35%. In HEK293 cell line apoptosis in control sample has the highest level and is about 20%, during incubation of HEK293 cell line with pAntp_p16 chimeric peptide for 24 hours, apoptosis increases to 60%.

Concentration of peptides was 40 .mu.M. Y-axis—% of apoptotic particles. FIGS. 20 and 21 show that both pAntp_p16 and Tat_p16 induce apoptosis in greater number of cells than in the control samples. The maximum level of apoptosis in the samples with peptides was observed 24 hours after incubation, however, it has been observed that although the level of apoptosis is increased depending on the incubation time, the increase in the number of apoptotic particles does not occur evenly. In the study of changes in the level of apoptosis depending on the time of incubation of samples with peptides we detected time intervals which are characterized by an increased formation of apoptotic bodies. Thus, during the incubation of the synchronized cell culture HEK293 with chimeric peptides pAntp_p16, points with an increased apoptosis are at 2 and 10 hours of incubation, whereas with the peptide Tat_p16 such points are at 6 and 16 hours of incubation (FIG. 21).

The presence of these time periods with increased apoptosis is characteristic for all cultures studied, and these "highs" for apoptosis of the tumor cell cultures are located at approximately the same time intervals and differ in the level of apoptosis (FIG. 21).

A—HEK293 cell line synchronized in G0/G1-phase after removal of the sync block and adding the study peptides.

B—A549 cell line synchronized in G0/G1-phase after removal of the sync block and adding the peptides to be investigated.

X-axis—incubation time, Y-axis—the number of apoptotic particles, %.

Example 6

Investigation of Influence of the Position and the Size of the Peptide Vector on the Antiproliferative Activity of Chimeric Peptides We used three versions of the chimeric peptide containing p16INK4a active center and pAntp vector. These chimeric peptides differ by location of the active center relative to N-C termini of the molecule and the presence of an insertion of 44 amino acids (SERKRGRQTYTRYQTLELEKEFHFNRYL-TRRRRIEIAHALCLTE, SEQ ID NO: 9) for peptide 3 produced by genetic engineering method (Table 1).

In the study of the properties of these peptides we also investigated synchronized and nonsynchronized cell cultures. In a synchronized culture, the peptide was added at the time of sync block removal and in the nonsynchronized at a monolayer density (for adhesion cultures) of .about.50%.

The results reflecting the change in cells distribution according to cell cycle phase for the peptide pAntp-p16INK4a (1, 2, 3) are shown in FIGS. 22 and 23. As is seen from FIG. 22, while adding the control peptide pAntp_zam to the synchronized and nonsynchronized cells, changes of the cell cycle phases in test samples do not differ from the control. Adding the chimeric peptide (1) (Table 1) containing the fragment p16INK4a, also fails to induce the expected cytostatic effect. For both synchronized and nonsynchronized cultures, cell distribution according to the phases of the cell cycle does not differ in comparison with the control. However, addition of peptides 2 and 3 causes a marked reduction in S-phase, while also increasing the number of cells in G0/1 phase. This trend is more pronounced in experiments on synchronized cultures.

Experiments carried out on cell line A549 (FIG. 23) revealed similar cell cycle changes for all the test peptides.

The results indicate that the chimeric peptide pAntp-p16INK4a (1) does not have an anti-proliferative effect on cells. At the same time, adding the chimeric peptide pAntp-p16INK4a (2 and 3) has an antiproliferative effect on cells and leads to an increase of cells in G1 phase.

Absence of a cytostatic effect after adding the chimeric peptide 1 is possibly due to conformational changes of the peptide molecule due to the position of the internalizable sequence pAntp at N-terminus of the chimeric peptide (in case of peptides 2 and 3, pAntp is located at C-terminus).

In the next phase of work, we assessed the dependence of the cytotoxic effect exerted by the chimeric test peptides with the peptide vector pAntp. An experiment to determine the level of apoptosis was carried out on the cell lines A549 (human, lung carcinoma), HEK293 (human, embryonic kidney) and MCF-7 (human, mammary adenocarcinoma). Cells were cultured by standard techniques in DMEM medium containing 10% of FSB. A part of the cells was previously synchronized using the method of double thymidine block and synchronization method with the depleted media (see "Experiment. Parts"). The chimeric test peptides pAntp-p16 (1 and 2) were added to the culture medium. As a negative control we used cells treated with the peptide pAntp_zam (FIGS. 24, 25).

As is seen from FIG. 24, 25, the level of apoptosis is not affected by the addition of the control peptide pAntp_zam, while the addition of pAntp-p16 (1, 2) markedly increases the number of cells entered apoptosis. Thereby, no differences in the magnitude of the effect depending on the cell type (for lines A549 and HEK 293) were revealed. Comparison of the effect of peptides pAntp-p 16 1 and 2 on the level of apoptosis in HEK293 cell line is shown in FIG. 26. FIG. 26 shows power dependency of the number of apoptotic bodies from the concentration of pAntp-p16.

Comparison of the level of apoptosis under addition of chimeric peptides showed that the level of apoptosis in the case of adding peptide 2 is almost two times higher than the level of apoptosis in the experiment with the chimeric peptide 1. A more pronounced cytotoxic effect was observed on the synchronized culture. Thus, it was found that the chimeric peptides pAntp 1 and 2 containing fragment p16INK4a possess a pronounced cytotoxic action on cell cultures.

When comparing cytotoxic and cytostatic effect of the chimeric peptides pAntp-p16 1 and 2, it can be concluded that the change in position of internalizable sequence pAntp in the chimeric peptide from C- to N-terminus leads to the disappearance of the cytostatic effect and decrease in cytotoxic effects.

Example 7

Study of Changes in the Number of Phosphorylated pRb in Cell Cultures Incubated with Chimeric Peptides One of the objectives of the study was to prove that anti-proliferative effects of test peptides are associated with a specific action by fragments of cyclin kinase inhibitors within their structure. Although the literature describes the retention of inhibiting properties of such peptides for phosphorylating function of cyclin-dependent kinases, these data were obtained from cell extracts. We conducted a study of changes in the level of phosphorylation of pRB—a molecular target of D-type cyclin kinases against the test peptides—including inhibiting the sequence from the corresponding protein inhibitors p21 and p16INK4a.

Activation of the cell's own p 16INK4a leads to inhibition of phosphorylation of pRb. Accumulation of underphosphorylated pRb leads to inhibition of E2F1 and decreases expression of cyclins A and B, which is one of the key mechanisms in the cell cycle interruption. The activity of p16 can be measured on an amount of phosphorylated pRb.

The flow cytometry method allows to visualize cells in which the pRb product is in "underphosphorylated" state. Fluorescently labeled antibodies react with "underphosphorylated" pRb. FIG. 27, A shows isotype control, designed to exclude non-specific fluorescence, B shows control sample in which some pRb cells are in underphosphorylated state.

To determine the amount of "underphosphorylated" pRb, we performed series of experiments with addition of the chimeric test peptides to the cell culture synchronized by the depleted medium method after removal of the sync block, and harvesting the cells every two hours. A part of the cells from every plate was fixed to further define the cell cycle phases, and a part was fixed by the procedure described under "Materials and Methods" to determine the amount of "underphosphorylated" pRb. Also, the samples of synchronized cells but without addition of peptides were used as a negative control. It has been shown that the addition of chimeric peptide to the cell culture inhibits the phosphorylation of pRb and reduces its maximum level in the culture (FIG. 28).

As is seen from FIG. 28, the initial level of "underphosphorylated" pRb is approximately the same in control and test samples, but after removal of the sync block in the samples without adding the chimeric peptide, its level starts to rise, and to a certain point (4 or 6 hours of incubation), depending on the cell line it reaches a maximum and then begins to decline. In the samples with the chimeric peptide, the level of the "underphosphorylated" pRb begins to increase later and reaches its peak after 8 hours of incubation, whereby this value being lower than in the control samples.

Example 8

Study of Change in the Level of mRNA Expression of Cyclin B Using RT-PCR Techniques It is known that the phosphorylation of pRb is an initiating step for activation of expression of cyclins A and B and for transition of cells from G1 into S phase of the cell cycle. Quantitative PCR method was used to study mRNA expression level of cyclin B when exposed to Tat_p16 peptide. For this purpose during experiment on synchronized culture with adding Tat_p16 chimeric peptide at a concentration of 40 .mu.mol, we performed a parallel selection of cells from samples for RNA extraction, whereas a part of the cells served the determination of the cell cycle phases. Further processing of the material involved RNA isolation and quantitative PCR reaction setting (RT-PCR) carried out according to the protocol.

FIG. 29 shows the change of the amount of cyclin B mRNA obtained by the quantitative PCR method, which reflects the change in the expression level of cyclin B, FIG. 29A. It also shows the change of the number of cells in G2/M-phase of the cell cycle obtained by the flow cytometry, FIG. 29B.

It can be appreciated from FIG. 29 that the chimeric peptide Tatp16 inhibits the expression of B cyclin and arrests the S-G2 transition accordingly. From the results shown in FIG. 14B it is seen that the number of cells in G2-phase in the control sample has its maximum of 12 hours of incubation, while for the sample with the peptide an increase in G2-phase occurs only after 16 hours of incubation. Figure A shows the changes in the expression level of cyclin B, it is seen that the control also has a maximum at 12 hours, which coincides with the maximum of cells in the G2-phase. In a sample with Tat_p16 peptide, the expression level increases after 16 hours of incubation. Addition of peptide results in a delay of cyclin B expression. Thus, it was confirmed that the observed cytotoxic effect is due to the influence on the phosphorylation process of pRb and as a consequence, on the inhibition of cyclin expression.

Example 9

Study of the Combined Action of the Chimeric Peptides and Chemotherapy

In clinical practice, cytostatics as chemotherapeutic agents are commonly used in the treatment of cancer. Their effect is based on the fact that the cells under their influence trapped in a certain phase of the cell cycle, and combined administration of a drug with cytotoxic activity in this phase of the cycle allows for the death of a great number of cells.

The chimeric test peptides have demonstrated the cytostatic and cytotoxic activity. Moreover, the cytostatic activity is specific and is the result of a direct effect of the peptide on the cell's genome. However, as shown above, the effect of the chimeric peptide on the cell culture is not sufficient to provide therapeutically significant results. As a result, it was proposed to study the combined effect of internalized peptides and chemotherapeutic agents.

We investigated the following chemotherapeutics affecting the cell cycle used in the clinical practice: Taxol causing a G2/M-phase arrest, Etoposide causing a S-phase arrest, and 5-fluorouracil causing a G0/G1-phase arrest of the cell cycle. The most informative results for the combined action of the chemotherapeutics and chimeric peptides were obtained with the peptide pAntp_p16 (2) (FIG. 33). In preliminary experiments on cell lines HEK293 and A549 we observed the expected effects of the cell cycle arrest in phases specific to each test drug and selected an optimal concentration, which allows to obtain the effect without causing total destruction of the cells. This concentration for all drugs was 100 nMol.

In the investigation of the combined effects of the chemotherapeutics and the chimeric peptide pAntp_p16 (2), enhancement of cytostatic effect was observed for formulations 5-fluorouracil, and etoposide: increase of the G0/G1 (FIG. 30A) and S (FIG. 30B) phase, respectively. During a co-incubation of the cells with Taxol and pAntp_p16 we observed the reduction in G2/M phase compared to the samples with Taxol, increase in G0/G1 phase (FIG. 30C), and an enhanced cytotoxic effect. FIG. 30 shows the change in the phase of the cell cycle in the combined action of chemotherapeutics and test peptides.

It was also shown that the combined use of chemotherapy and the chimeric test peptides enhanced the cytotoxic effect. During the incubation of the cells with chemotherapeutic drugs and chimeric peptide there is an increase in the level of apoptosis relative to the level of apoptosis in the samples only treated with chemotherapeutics. We also detected the level of the cell death, which was calculated based on the amount of living cells in the samples using the Goryaev chamber. The level of the dead (perished) cells increases in samples incubated with chemotherapeutic drugs and with the test peptide.

FIG. 31 shows the results of the cytotoxic effects of the combined use of chemotherapeutics and pAntp_p16 chimeric peptide (2).

In the study of the combined effects of chemotherapeutics and the test peptides pAntp_p16, it was found that there is a significant enhancement of cytotoxic activity of test chemotherapeutic drugs. The combined cytotoxic effect directly correlates with the nature of the cytotoxic effect of chemotherapy.

Example 10

Investigation of Anti-Tumor Activity of Chimeric Peptide p16_pAntp In Vivo (Local Injection)

Mice without thymus (nude) were used for investigation of the antitumor activity of the internalizable chimeric peptide p16_pAntp.

The mice were transplanted with human tumor cell culture lines A549 and HCT-116 in an amount of about 1 million cells per mouse. 39 mice were transplanted with A549 cells, of which 20 mice formed a control group, which later received a placebo. 10 mice constituted the 1st treatment group. After the formation of palpable tumors (4 days after inoculation of cells), they were injected directly into the tumor with a test peptide in a dose of 0.1 mg. 9 mice were the 2nd experimental group, they were also injected with 0.2 mg of the peptide into the tumor interior after the formation of the tumor site on day 4 of the transplantation. The peptide in the experimental groups was injected once every two days. The experiment lasted 24 days.

In the experimental groups, we observed a reduced tumor growth and on day 6 after the begin of administration of the peptide there could be observed a significant reduction in tumor volume in experimental groups compared with the control ones (FIG. 32). The experiment lasted 24 days. During this time, we performed 10 injections of the chimeric peptide in the experimental groups. In the control group, on day 24 of the experiment, the average tumor volume in mice was 95.24 mm.sup.3, one mouse died. In the first experimental group (administered dose of peptide—0.1 mg) average tumor volume was 39.29 mm.sup.3, one mouse died. In the second experimental group (administered dose of peptide—0.2 mg), the average tumor volume was 57.51 mm.sup.3, but no animals died.

When administered to the mice the transplanted human culture HCT-116, the animals were divided into two groups: a control group of 10 mice that were not subsequently administered with the test peptide and a test group (10 mice) that was treated with the chimeric test peptide p16_pAntp at a dose of 0.1 mg to the tumor site. The experiment lasted 28 days, 11 peptide injections were done to the test group, the first injection was made on day 6 after the tumor cell transplantation.

The tumor nodule of HCT-116 cells is characterized by a large in size and the presence of ulceration. In the control group, on day 28 of the experiment the average tumor volume reached 679 mm.sup.3, 3 mice died during the experiment. In the test group, a lower rate of tumor growth was observed (FIG. 32), on day 28 of the experiment the average tumor volume was 225.4 mm.sup.3, the number of dead animals in the experimental group was 2.

FIG. 32 shows pairs of mice from different groups after 7 injections of the test peptide. A significant reduction of the tumor nodule in the experimental groups is observed.

Thus, the local administration of the chimeric peptide p16-pAntp leads to a significant (more than 50%) growth inhibition of experimental models of human tumors (breast cancer, colorectal cancer).

Example 11

Study of Cytotoxic Properties of Chimeric Peptides on Short-Term Cultures of Human Tumors We investigated the antitumor activity of chimeric peptides comprising internalizable fragment Antp and functional fragments of the cyclin kinase p16INK4a inhibitors (DAAREG-FLDTLVVLHRAGAR-S-RQIKIWFQNRRMKWKK (SEQ ID NO. 3)). 150 mg of the peptide p16-pAntp were synthesized using the solid phase synthesis method (see section Methods). To study the effects on human tumors, we used the method of short-term cultures.

Method of obtaining short-term cultures of tumors from surgical specimens. Short-term cultures were obtained from surgical specimens. Sampling of the area for preparation of the culture was carried out in as soon as possible after surgery and with the participation of the pathologist. The excised tissue portion measured in average 1.5 cm.sup.3. The tissue was disintegrated mechanically, a cell suspension was placed in RPMI medium, containing 5% FBS. After 24 hours incubation at 37.degree. C. and 5% CO.sub.2, the medium was replaced with the medium containing the chimeric peptide (p16_pAntp in concentration of 40 .mu.mol) or it was replaced with Taxol in concentration of 100 nmol or 500 nmol, containing both peptide and Taxol for a number of experiments. In control samples, the medium was replaced by fresh one. Recorded first point was 0 hours.

Incubation took place at 37.degree. C. and 5% CO.sub.2 for 24 hours, for a number of experiments the incubation time 24 and 48 hours.

The results were evaluated by flow cytometry using double staining of samples with AnnexinV-PI and staining of fixed material with PT. We assessed level of particles positive for AnnexinV (early apoptosis), the level of particles positive for the double labeled AnnexinV-PI (late apoptosis), the amount of particles in the non-fixed samples capable to take up PI (necrosis), the distribution of the cells in phases of the cell cycle, level of subdiploid peak (amount of particles of fragmented DNA, apoptosis). In order to detect apoptosis of epithelial cells we used a double staining of the cytokeratin-FITC-PI antibody (FIG. 34).

In total, 126 tissue samples analyzed: 63 of them were pathologic tissue samples (and 63 samples of normal tissues as controls). Out of 63 pathological specimens, 47 tumors of malignant tumor genesis were investigated (10 breast cancer, 15 kidney cancer, 6 uterine cancer, 4 prostate cancer, 3 ovarian cancer and lung cancer, and 2 cases for each gastric cancer, pancreatic cancer, bladder cancer). Also we examined fibroadenoma tissue samples (N=9), as well as 7 mammary tissue samples with simple ductal hyperplasia.

The level of apoptosis was analyzed in 24 and 48 hours after the addition of peptides at a concentration of 40 A part of the experiments was conducted to examine the combined cytotoxic effects on tumor cells for traditional chemotherapeutic drugs and the peptide p16 pAntp.

Example 12

Investigation of antitumor activity of the peptide p16_pAntp. Summarized results for peptide p16_pAntp cytotoxic activity are shown in Table 3.

TABLE 3

Average level of induced apoptosis in short-term cultures of tumors when exposed to the peptide p16_Antp. (24 hours, 40 μM)

|  | Induced apoptosis level |
| --- | --- |
| Breast cancer | 25.8 |
| Kidney cancer | 26.0 |
| Cervix cancer | 5.2 |
| Pancreas cancer | 18.9 |
| Lung cancer | 13.5 |
| Stomach cancer | 35.4 |
| Prostate cancer | 15.4 |
| Bladder cancer | 24.7 |
| Ovarian cancer | 12.3 |

The analysis of the results shows that the types of cancer most sensitive to the cytotoxic effect of the peptide p16_pAntp are renal, breast, gastric, and bladder cancers. It should be noted that the short-term cultures of bladder cancer are characterized by very high levels of spontaneous apoptosis (60-70%). Although the addition of the peptide increases this level slightly, this fact may cause the results to be non-representative.

Example 13

Investigation of the cytotoxic effect on the cells of the breast fibroadenoma. Samples of fibroadenoma of the breast tissue were investigated. In a short-term culture of these cells having a low levels of spontaneous apoptosis (maximum 20%, average 12.8%), p16 peptide had a significant cytotoxic effects and induced marked apoptosis after 24 hours with the average level of 38.2% to a maximum of 80%.

A less pronounced cytotoxic effect was found for the breast cancer cells showing signs of a simple ductal hyperplasia (mean induced apoptosis of 14.5%). These results are consistent with data obtained by the author on study of the ratio of proliferation activity to the level of spontaneous apoptosis in abnormal breast tissues. It was shown that the ratio of the spontaneous proliferation to the apoptosis was the highest for fibroadenoma tissue, breast cancer cells are on the second place, followed by simple ductal hyperplasia and the normal breast tissue. If one of the factors determining the sensitivity of the cells to the cytotoxic effects of the peptides containing the inhibitors of proliferation is the activity of cell division, then the fibroadenoma cells' sensitivity to the peptide p16_pAntp is quite logical.

The observed effect of sensitivity of benign proliferative processes in the breast tissue may be promising for their treatment. Results of local administration of the peptides for treatment of transplantable solid tumors suggest their efficacy when administered locally in the area of benign proliferative processes in breast tissues.

The obtained results revealed a range of human tumors sensitive to the peptide p16_pAntp. It has been found that such locations as breast cancer, colorectal cancer, gastric cancer, bladder cancer, kidney cancer are promising targets for further study of cytotoxic (antitumor) actions of the test peptide. These results are novel because in the available literature, there is no data on the effect of the peptide on the analyzed human tumors.

The invention claimed is:

1. A pharmaceutical composition, comprising:
   a) a chimeric peptide comprising a functional sequence of protein inhibitor of cyclin kinase p16INK4a (SEQ ID NO: 1) or p21/CIP/KIP (SEQ ID NO: 6) and a transport sequence, wherein the functional sequence and the transport sequence are linked by a group X, wherein X represents an amino acid sequence comprising from 1 to 50 amino acid residues, and wherein the chimeric peptide has the amino acid sequence of SEQ ID NO: 3, SEQ ID NO: 4, SEQ ID NO: 7, or SEQ ID NO: 8;
   b) a therapeutically active agent selected from the group consisting of 5-fluorouracil and etoposide;
   c) a pharmaceutically acceptable carrier.

2. The pharmaceutical composition according to claim 1, wherein the chimeric peptide has the amino acid sequence of SEQ ID NO: 8.

3. The pharmaceutical composition according to claim 1, wherein the chimeric peptide has the amino acid sequence of SEQ ID NO: 3.

4. The pharmaceutical composition according to claim 1, wherein the chimeric peptide has the amino acid sequence of SEQ ID NO: 4.

5. The pharmaceutical composition according to claim 1, wherein the chimeric peptide has the amino acid sequence of SEQ ID NO: 7.

6. The pharmaceutical composition according to claim 1, wherein the chimeric peptide is in the amount of up to 400 mg/kg.

7. A method of treating a hyperproliferative disease comprising administering to a mammal in need of such treatment the pharmaceutical composition according to claim 1.

8. The method according to claim 7, wherein the hyperproliferative disease is cancer.

9. The method according to claim 8, wherein the cancer is selected from the group consisting of colorectal cancer, renal cancer, lung cancer, breast cancer, bladder cancer, pancreatic cancer, uterine cancer, prostate cancer, gastric cancer and ovarian cancer.

10. The method according to claim 8, wherein the cancer is renal cancer, breast cancer, gastric cancer or bladder cancer.

* * * * *